US008163475B2

(12) United States Patent
Konradi

(10) Patent No.: US 8,163,475 B2
(45) Date of Patent: Apr. 24, 2012

(54) METHODS FOR DIAGNOSIS AND PROGNOSIS OF PSYCHOTIC DISORDERS

(75) Inventor: Christine Konradi, Nashville, TN (US)

(73) Assignee: The McLean Hospital Corporation, Belmont, MA (US)

( * ) Notice: Subject to any disclaimer, the term of this patent is extended or adjusted under 35 U.S.C. 154(b) by 763 days.

(21) Appl. No.: 11/804,461

(22) Filed: May 18, 2007

(65) Prior Publication Data

US 2008/0009010 A1 Jan. 10, 2008

Related U.S. Application Data

(60) Provisional application No. 60/801,313, filed on May 18, 2006, provisional application No. 60/928,151, filed on May 7, 2007.

(51) Int. Cl.
C12Q 1/68 (2006.01)
C12Q 1/00 (2006.01)
G01N 33/566 (2006.01)
G01N 33/567 (2006.01)

(52) U.S. Cl. ............... 435/6; 435/4; 436/501; 436/504

(58) Field of Classification Search .................. None
See application file for complete search history.

(56) References Cited

U.S. PATENT DOCUMENTS

| | | |
|---|---|---|
| 5,474,796 A | 12/1995 | Brennan |
| 5,494,794 A | 2/1996 | Wallace |
| 5,541,308 A | 7/1996 | Hogan et al. |
| 6,040,138 A | 3/2000 | Lockhart et al. |
| 6,104,943 A | 8/2000 | Frederick et al. |
| 6,400,978 B1 | 6/2002 | Teicher et al. |
| 6,444,431 B1 | 9/2002 | Moser et al. |
| 6,582,908 B2 | 6/2003 | Fodor et al. |
| 2004/0248286 A1 | 12/2004 | Konradi et al. |
| 2006/0051786 A1* | 3/2006 | Akil et al. .................. 435/6 |
| 2006/0099578 A1 | 5/2006 | Wallace et al. |
| 2008/0187911 A1 | 8/2008 | Papaconstantinou et al. |

OTHER PUBLICATIONS

DiMauro et al., "Mitochondrial Respiratory-chain Diseases," *N. Engl J Med.* 348:2656-2668 (2003).
Doniger et al., "MAPPFinder: Using Gene Ontology and GenMAPP to Create a Global Gene-expression Profile From Microarray Data," *Genome Biol.* 4:R7 (2003).
Heckers et al., "Differential Hippocampal Expression of Glutamic Acid Decarboxylase 65 and 67 Messenger RNA in Bipolar Disorder and Schizophrenia," *Arch Gen Psychiatry.* 59:521-529 (2002).
Kato et al., "Mitochondrial Dysfunction in Bipolar Disorder," *Bipolar Disord.* 2:180-190 (2000).
Kato et al., "Alterations in Brain Phosphorous Metabolism in Bipolar Disorder Detected by in Vivo $^{31}$P and $^{7}$Li Magnetic Resonance Spectroscopy," *J Affect Disord.* 27:53-59 (1993).
Kato et al., "Magnetic Resonance Spectroscopy in Affective Disorders," *J Neuropsychiatry Clin Neurosci.* 10:133-147 (1998).
Konradi et al., "Molecular Evidence for Mitochondrial Dysfunction in Bipolar Disorder," *Arch Gen Psychiatry.* 61:300-308 (2004).
Konradi et al., "Molecular Evidence for Mitochondrial Dysfunction in Bipolar Disorder," *Biol Psychiatry.* 59:10s (2006).
Kowaltowski et al., "Effect of Bcl-2 Overexpression on Mitochondrial Structure and Function," *J Biol Chem.* 277:42802-42807 (2002).
Le-Niculescu et al., "Identifying Blood Biomarkers for Mood Disorders Using Convergent Functional Genomics," *Mol Psychiatry.* 14:156-174 (2009).
Li et al., "Model-based Analysis of Oligonucleotide Arrays: Expression Index Computation and Outlier Detection," *Proc Natl Acad Sci U S A.* 98:31-36 (2001).
MacDonald et al., "Antipsychotic Drugs Elevate mRNA Levels of Presynaptic Proteins in the Frontal Cortex of the Rat," *Biol Psychiatry.* 57(9):1041-1051 (2005).
Naydenov et al., "Differences in Lymphocyte Electron Transport Gene Expression Levels Between Subjects with Bipolar Disorder and Normal Controls in Respose to Glucose Deprivation Stress," *Arch Gen Psychiatry.* 64(5):555-564 (2007).
Ohmori et al., "Assessment of Human Stress and Depression by DNA Microarray Analysis," *J Med Invest.* 52 Suppl.:266-271 (2005).
Smeitink et al., "Nuclear Genes of Human Complex I of the Mitochondrial Electron Transport Chain: State of the Art," *Hum Mol Genet.* 7:1573-1579 (1998).
Strakowski et al., "Neuroimaging in Bipolar Disorder," *Bipolar Disord.* 2:148-164 (2000).
van den Heuvel et al., "Demonstration of a New Pathogenic Mutation in Human Complex I Deficiency: a 5-bp Duplication in the Nuclear Gene Encoding the 18-kD (AQDQ) Subunit," *Am J Hum Genet.* 62:262-268 (1998).
van den Heuvel et al., "The Oxidative Phosphorylation (OXPHOS) System: Nuclear Genes and Human Genetic Diseases," *Bioessays* 23:518-525 (2001).
International Search Report mailed Oct. 29, 2007 (PCT/US07/12007). Cataldo et al., "Abnormalities in mitochondrial structure in cells from patients with bipolar disorder," *Am J Pathol.* 177:575-85, 2010.
Kato et al., "Comprehensive gene expression analysis in bipolar disorder," *Can J Psychiatry.* 52:763-71, 2007.
Zahn et al., "Transcriptional profiling of aging in human muscle reveals a common aging signature," *PLoS Genet.* 2:e115, 2006.

* cited by examiner

*Primary Examiner* — Olga N Chernyshev
(74) *Attorney, Agent, or Firm* — Clark & Elbing LLP

(57) ABSTRACT

The invention features methods diagnostic of a psychotic disorder such as bipolar disorder or schizophrenia. The methods include obtaining a cell sample from a subject, subjecting a cell from the sample to stress (e.g., nutrient stress), and measuring nucleic acid or polypeptide expression in the cell, where an alteration in expression is indicative of the subject having or being at increased risk of developing a psychotic disorder. The invention also features prognostic monitoring methods for subjects having a psychotic disorder, useful in determining the progression of a psychotic disorder in a subject or the effectiveness of a therapy.

5 Claims, 14 Drawing Sheets
(3 of 14 Drawing Sheet(s) Filed in Color)

Figures 1A(I)-1A (IV)

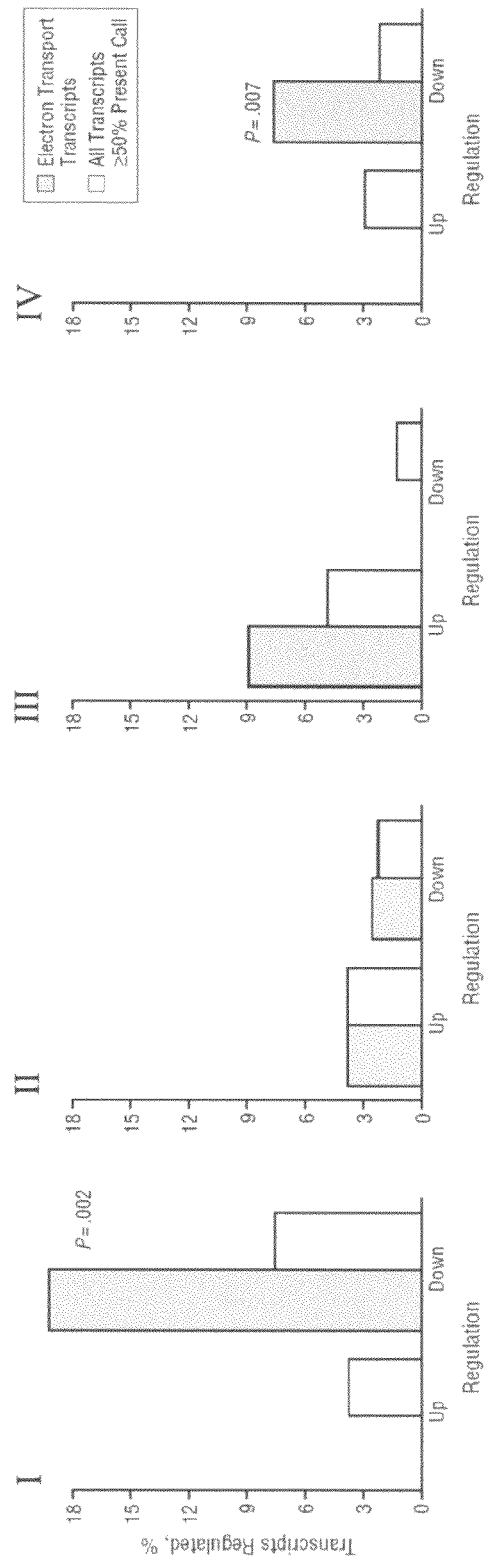
Figures 1B(I)-1B(IV)

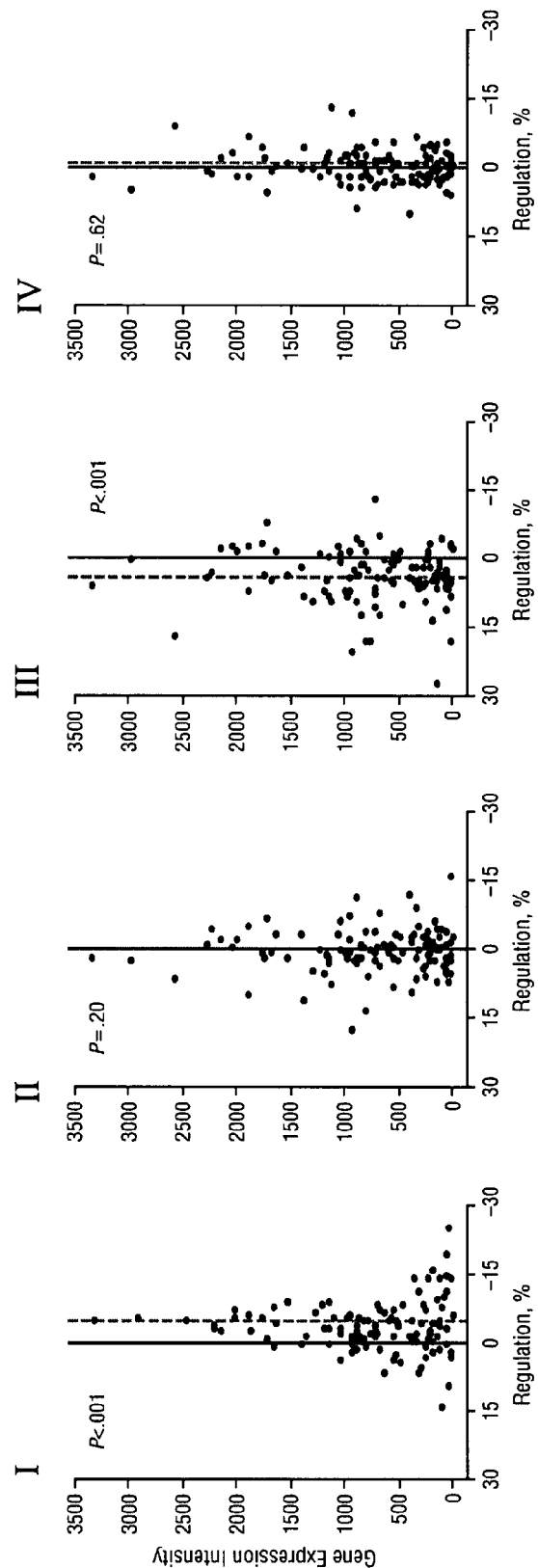
Figures 1C(I)-1C(IV)

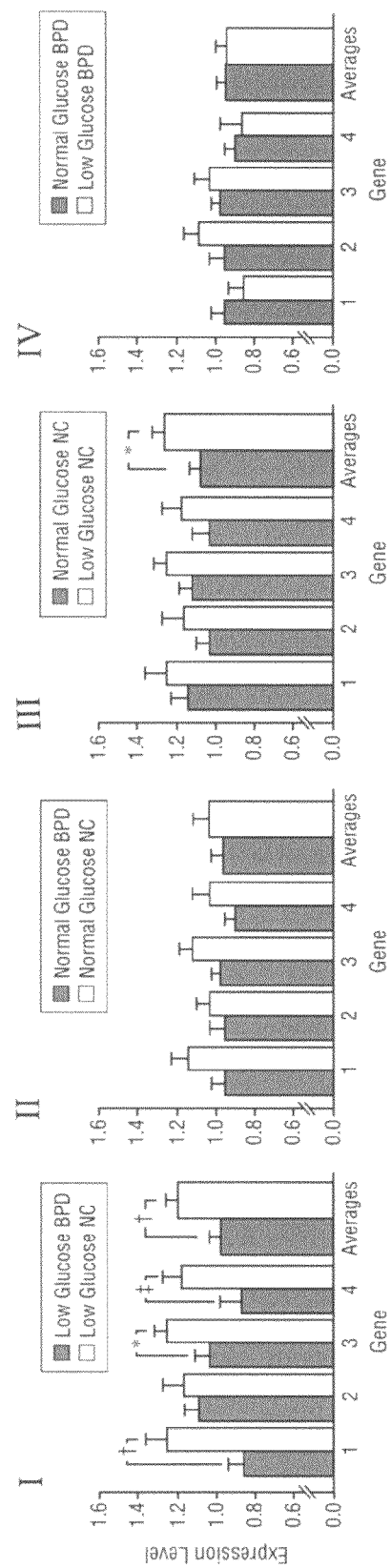
Figures 1D(I)-1D(IV)

Sample Information for Subjects with Bipolar Disorder and Normal Controls

| Subject No. | Diagnosis | Current Episode | Inpatient | Psychosis | Sex | Age y | Medications | MPE y | YMRS Score | BDI Score | Tests* GL | GN | PL | PN | FL |
|---|---|---|---|---|---|---|---|---|---|---|---|---|---|---|---|
| | | | | | | | Patients with Bipolar Disorder | | | | | | | | |
| 1 | BP-I | Manic | Yes | None | M | 53 | Lithium carbonate, 900 mg/d; synthroid, 100 μg/d; VPA, 1500 mg/d; ω-3 fatty acids, 1 g/d; quetiapine fumarate, 850 mg/d | 16 | 1 | 0 | X | | | | |
| 2 | BP-I | Manic | Yes | AH | F | 54 | Quetiapine fumarate, 300 mg/d; lithium carbonate 600 mg/d; buspirone hydrochloride, 10 mg/d | Unk | 30 | 12 | X | | X | | |
| 3 | BP-I | Manic | Yes | Delusions + AH | M | 22 | Risperidone (Risperdal Consta) 25 mg every 2 wk; risperidone, 6 mg/d; haloperidol, 5 mg/d; lithium carbonate, 1500 mg/d; lorazepam, 3 mg/d; benztropine mesylate, 2 mg/d† | Unk | 14 | 3 | X | X | X | X | |
| 4 | BP-I | Mixed | Yes | None | M | 44 | ω-3 fatty acids, 1 g/d; oxcarbazepine, 600 mg/d; fluoxetine hydrochloride, 20 mg/d; trazodone hydrochloride, 150 mg/d; | 15 | 1 | 34 | X | X | X | X | X |
| 5 | BP-I | Manic | Yes | None | M | 49 | Aripiprazole, 2 mg/d; lithium carbonate, 600 mg/d; | Unk | 18 | 26 | X | X | X | X | X |
| 6 | BP-I | None | No | None | M | 50 | Valproate extended release, 500 mg/d; fluoxetine hydrochloride, 10 mg/d; topiramate, 200 mg/d; ω-3 fatty acids, 1800 mg/d; propoxyphene napsylate–acetaminophen (Darvocet), 5 tablets/d | 12 | ND | 1 | X | X | X | X | X |
| 7 | BP-II | None | No | None | F | 50 | Lithium carbonate, 300 mg/d; sertraline hydrochloride, 100 mg/d; topiramate, 25 mg/d | 15 | 1 | 8 | X | X | X | X | |
| 8 | BP-I | Manic | Yes | None | F | 39 | Lithium carbonate, 1000 mg/d; olanzapine, 2.5 mg/d; | 15 | 6 | 0 | X | X | | X | X |
| 9 | BP-I | None | Yes | Delusions | F | 37 | Carbamazepine, 500 mg/d; fluoxetine hydrochloride, 80 mg/d; venlafaxine hydrochloride, 37.5 mg/d; | 12 | 2 | 15.5 | X | X | | X | X |
| 10 | BP-I | Depressed | Yes | AH | M | 19 | Lorazepam, 3 mg/d | 12 | 10 | 9.5 | X | X | | | X |
| 11 | BP-I | Depressed | Yes | Delusions | F | 39 | Carbamazepine, 600 mg/d; bupropion hydrochloride, 400 mg/d; lorazepam, 3 mg/d; quetiapine fumarate, 150 mg/d | 18 | 3 | 33.5 | | X | X | X | |
| 12 | BP-I | None | No | None | F | 42 | Escitalopram oxalate, 20 mg/d; VPA, 1000 mg/d; levothyroxine sodium (Synthroid), 112 μg/d‡ | 12 | 2 | 33 | X | X | X | X | X |
| 13 | BP-I | None | No | None | F | 47 | Aripiprazole, 20 mg/d; clonazepam, 0.5 mg/d; paroxetine hydrochloride, 60 mg/d; clonidine hydrochloride, 0.02 mg/d; | 12 | 1 | 26 | X | X | X | X | X |
| 14 | BP-I | None | No | None | M | 48 | Gabapentin, 1800 mg/d; venlafaxine hydrochloride, 75 mg/d | Unk | 2 | 30 | X | X | X | X | |
| 15 | BP-I | None | No | None | F | 34 | Venlafaxine hydrochloride, 300 mg/d; quetiapine fumarate, 100 mg/d; oxcarbazepine, 300 mg/d | 12 | 0 | 42 | X | X | X | X | X |
| 16 | BP-I | None | Yes | Delusions + AH | M | 43 | VPA, 1000 mg/d; olanzapine, 10 mg/d | 12 | 6 | 13 | | X | X | X | X |
| 17 | BP-I | None | No | Delusions + AH | F | 34 | Levatiracetam, 1000 mg/d | 16.5 | 9 | 8 | | | X | X | X |

Figure 2 (page 1 of 2)

| Subject No. | Diagnosis | Current Episode | Inpatient | Psychosis | Sex | Age, y | Medications | MPE, y | YMRS Score | BDI Score | Tests* GL | GN | PL | PN | FL |
|---|---|---|---|---|---|---|---|---|---|---|---|---|---|---|---|
| 18 | BP-II | None | Yes | None | F | 49 | Sibutramine hydrochloride, 15 mg/d; bupropion hydrochloride sustained release, 400 mg/d; zonisamide, 400 mg/d; clonazepam, 3 mg/d; vigabatrin, 8 mg/d; lamotrigine, 500 mg/d; pramipexole dihydrochloride, 1.5 mg/d; gabapentin, 1200 mg/d; | 5 | 3 | 13 | X | X | | | |
| 19 | BP-I | None | Yes | None | M | 26 | Oxcarbazepine, 450 mg/d; gabapentin, 1200 mg/d; escitalopram oxalate, 15 mg/d; lamotrigine, 200 mg/d; | 18 | 1 | 6 | | | X | X | X |
| 20 | BP-I | None | Yes | None | M | 23 | Lamotrigine, 450 mg/d; perphenazine, 4 mg/d; fluoxetine hydrochloride, 20 mg/d; zolpidem tartrate, 10 mg/d; fexofenadine hydrochloride, 180 mg/d; lorazepam, 1 mg/d; | 15 | 3 | 22 | | | X | X | X |
| 21 | BP-II | None | No | None | F | 49 | None | 19 | 3 | 12 | | | X | X | |
| Entire group with bipolar disorder | | | | | | Mean 40.5 | | Mean 13.9 | Mean 5.8 | Mean 16.5 | 15 | 15 | 16 | 17 | 13 |

| Subject No. | Diagnosis | Current Episode | Inpatient | Psychosis | Sex | Age, y | Medications | MPE, y | YMRS Score | BDI Score | Tests* GL | GN | PL | PN | FL |
|---|---|---|---|---|---|---|---|---|---|---|---|---|---|---|---|
| | | | | | | | NC Subjects | | | | | | | | |
| 1 | NC | | | | F | 34 | | 19 | | | X | X | X | X | X |
| 2 | NC | | | | F | 23 | | 16 | | | X | X | X | | X |
| 3 | NC | | | | M | 28 | | Unk | | | X | X | X | X | X |
| 4 | NC | | | | M | 35 | | Unk | | | X | X | X | X | |
| 5 | NC | | | | M | 21 | | 17 | | | | X | | X | X |
| 6 | NC | | | | M | 22 | | 16 | | | X | X | | X | X |
| 7 | NC | | | | M | 23 | | 15 | | | X | X | X | | |
| 8 | NC | | | | M | 47 | | 10 | | | X | | X | X | X |
| 9 | NC | | | | F | 23 | | 14 | | | | X | | X | X |
| 10 | NC | | | | M | 46 | | 13 | | | | | | X | X |
| 11 | NC | | | | F | 57 | | 12 | | | | X | X | X | X |
| 12 | NC | | | | M | 59 | | 14 | | | X | X | X | X | X |
| 13 | NC | | | | M | 30 | | 14 | | | X | | | X | X |
| 14 | NC | | | | F | 43 | | 14 | | | X | | | X | X |
| 15 | NC | | | | M | 53 | | 12 | | | | | X | X | X |
| 16 | NC | | | | M | 52 | | 18 | | | | | | X | |
| 17 | NC | | | | M | 54 | | 12 | | | | | | X | X |
| 18 | NC | | | | F | 36 | | 12 | | | | | X | | |
| 19 | NC | | | | F | 46 | | 11 | | | X | X | | | |
| 20 | NC | | | | F | 57 | | 13 | | | | | X | | |
| 21 | NC | | | | F | 36 | | 14 | | | | | X | X | |
| Entire NC group | | | | | | Mean 39.3 | | Mean 14 | | | 10 | 11 | 15 | 16 | 12 |

Abbreviations: AD, antidepressants; AH, auditory hallucinations; BDI, Beck Depression Inventory; BP-I, bipolar I disorder; BP-II, bipolar II disorder; FL, fresh lymphocytes; GL, low-glucose gene arrays; GN, normal-glucose gene arrays; NC, normal control; ND, not determined; MPE, medium parental education; PL, low-glucose quantitative polymerase chain reaction; PN, normal-glucose quantitative polymerase chain reaction; VPA, valproic acid; YMRS, Young Mania Rating Scale.
*X denotes that the test was performed for the individual. No entry indicates that the test was not performed for the individual.
†Risperdal Consta is manufactured by Alkermes, Inc, Cambridge, Mass.
‡Synthroid is manufactured by Abbott Laboratories, Abbott Park, Ill.

Figure 2 (page 2 of 2)

METHODS FOR DIAGNOSIS AND PROGNOSIS OF PSYCHOTIC DISORDERS

CROSS-REFERENCE TO RELATED APPLICATIONS

This application claims benefit of U.S. Provisional Application No. 60/801,313, filed May 18, 2006, and U.S. Provisional Application No. 60/928,151, entitled "Methods for Diagnosis and Prognosis of Psychotic Disorders," filed May 7, 2007, Inventor Christine Konradi. Each of these applications is hereby incorporated by reference.

BACKGROUND OF THE INVENTION

The invention relates to diagnostic and prognostic methods for psychotic disorders such as bipolar disorder, schizophrenia, and other disorders characterized by abnormal expression of metabolic genes.

Psychotic disorders such as bipolar disorder (BPD) are among the top ten causes of disability worldwide. BPD, in particular, is responsible for a national annual economic burden of over $40 billion (estimated in 1991). While the etiology of BPD and other psychotic disorders such as schizophrenia remain largely unknown, recent findings point to a disturbed mitochondrial energy metabolism in such subjects.

BPD causes dramatic mood swings, affects between 1 to 3% of the population in the US and is associated with high risk of suicide. In the case of BPD, recent studies have shown decreased hippocampal (HIP) and dorsolateral prefrontal cortex (PFC) levels of creatine kinase mRNA, as well as decreased levels of high-energy phosphates in the frontal and temporal lobes of BPD patients, providing support for the idea that mitochondrial energy metabolism plays an important role in the etiology of the disease. Previously, a downregulation in nuclear mRNA coding for mitochondrial electron transport proteins in post-mortem hippocampal tissue from patients with BPD had been reported.

BPD, along with other psychotic disorders such as schizophrenia, are diagnosed based on the course of symptoms and family history, but the etiology of such disorders remains elusive. Previously, no clinical tests existed to verify diagnosis. Thus, there is a need for improved diagnostic and prognostic techniques for psychotic disorders.

SUMMARY OF THE INVENTION

The present invention features methods for diagnosing subjects with a psychotic disorder and prognostic methods for monitoring the progression or improvement of a subject having a psychotic disorder.

Accordingly, in a first aspect the invention features a method for diagnosing a psychotic disorder (e.g., bipolar disorder, schizophrenia, or any psychotic disorder described herein) or propensity thereto in a subject including the steps of (a) obtaining a cellular sample, for example, a fluid sample (e.g., a blood sample) or tissue sample, from the subject; (b) subjecting a cell from the sample to stress, for example, nutrient stress (e.g., glucose stress), oxygen stress, temperature stress, or osmotic stress; and (c) measuring expression in the cell of at least one (e.g., 2, 3, 4, 5, 7, 10, 15, 25, 50, or 100) nucleic acid(s) or polypeptide(s) listed in Table 3, FIGS. 1A(I)-1A(IV), or FIGS. 6A-6D where an alteration (e.g., a decrease) in the expression as compared to the expression in a corresponding cell from a cell sample taken from a control subject is indicative of the subject having a psychotic disorder or propensity thereto. In one embodiment, the cell sample includes a lymphocyte. In another embodiment, step (b) subjecting includes culturing the cell.

In a second aspect, the invention features, a method for diagnosing a psychotic disorder (e.g., bipolar disorder, schizophrenia, or any psychotic disorder described herein) or propensity thereto in a subject, including the steps of (a) obtaining a cell sample, for example, a fluid sample (e.g., a blood sample) or tissue sample, from the subject; (b) subjecting a cell from the sample to stress, for example, nutrient stress (e.g., glucose stress), oxygen stress, temperature stress, or osmotic stress; and (c) measuring the level of expression in the cell of at least one (e.g., 2, 3, 4, 5, 7, 10, 15, 25, 50, or 100) mitochondrial energy metabolism nucleic acid(s) or polypeptide(s), where an alteration (e.g., a decrease) in the level of expression as compared to the expression in a cell from a sample obtained from a control subject is indicative of the subject having a psychotic disorder or propensity thereto. In one embodiment, the cell sample includes a lymphocyte. In another embodiment, step (b) subjecting includes culturing the cell.

The invention also features prognostic methods for monitoring a psychotic disorder (e.g., bipolar disorder, schizophrenia, or any psychotic disorder described herein) in a subject having the disorder. The method including the steps of (a) obtaining a cell sample from the subject; (b) subjecting a cell from the sample to stress, for example, nutrient stress (e.g., glucose stress), oxygen stress, temperature stress, or osmotic stress; (c) measuring the level of expression in the cell of (i) at least one (e.g., 2, 3, 4, 5, 7, 10, 15, 25, 50, or 100) mitochondrial energy metabolism nucleic acid(s) or polypeptide(s) or (ii) at least one (e.g., 2, 3, 4, 5, 7, 10, 15, 25, 50, or 100) nucleic acid(s) or polypeptide(s) from in Table 3, FIGS. 1A(I)-1(A)(IV), or FIGS. 6A-6D; and (d) repeating steps (a)-(c) within five years, two years, or one year (e.g., within 6 months, 3 months, 2 months, one month, two weeks, or one week), thereby providing a second measurement of expression, where an alteration in the second measurement as compared to the level measured in step (c) is indicative of the progression of the psychotic disorder in the subject. The method may further include, between steps (c) and (d), a step of administering a therapy such as an anti-psychotic (e.g., those described herein) to the subject (e.g., where the therapy was not administered to the subject within two years, one year, or six months (e.g., within 6 months, 3 months, 2 months, one month, two weeks, or one week) prior to performing step (a))).

By "subject" is meant either a human or non-human mammal.

By "control subject" is meant a subject that does not have a psychotic disorder.

By "stress," in the context of stressing cells, is meant any condition resulting in a physiological strain on the cells as compared to standard cell culture conditions, as are known in the art. In some embodiments, these conditions include a reduced concentration of an essential nutrient (e.g., decreased glucose or sucrose concentrations), either increased or decreased oxygen conditions (e.g., as described herein), either increased or decreased temperature (e.g., as described herein), or either increased or decreased osmolarity (e.g., as described herein).

By "biological sample" is meant any sample of biological origin or containing, or potentially containing, biological particles. In certain embodiments, biological samples are cellular samples.

By "blood component" is meant any component of whole blood, including host red blood cells, white blood cells (e.g., lymphocytes), and platelets. Blood components also include the components of plasma, e.g., proteins, lipids, nucleic acids, and carbohydrates.

By "cellular sample" is meant a sample containing cells or components thereof. Such samples include tissue samples (e.g., samples taken by biopsy from any organ or tissue in the body) and naturally occurring fluids (e.g., blood, lymph, cerebrospinal fluid, urine, cervical lavage, and water samples), portions of such fluids, and fluids into which cells have been introduced (e.g., culture media, and liquefied tissue samples). The term also includes a lysate. Any means for obtaining such a sample may be employed in the methods of the invention; the means by which the sample is obtaining is not critical to the invention.

By "alteration in expression" is meant a change in expression level of a nucleic acid or polypeptide. This difference may be either an increase or a decrease in expression when compared to a control or baseline (e.g., a previous measurement). In certain embodiments, the increase or decrease is at least 10%, 20%, 30%, 40%, 50%, 60%, 70%, 80%, 90%, or 100%. An increase may further be at least 125%, 150%, 200%, 300%, or 500%.

By "psychotic disorder" is meant a mental disorder characterized by psychosis which may involve cognitive problems, delusions, or hallucinations. Psychotic disorders include, without limitation, bipolar disorder, schizophrenia, schizoaffective disorder, schizophreniform disorder, shared psychotic disorder, and brief psychotic disorder.

By "a bipolar disorder" is meant a mood or affective disorder characterized by pathological mood swings from mania to depression. The diagnostic criteria for a bipolar disorder (e.g., bipolar I: mania and depression; bipolar II: hypomania and depression; bipolar III: cyclothymic disorders; bipolar IV: hypomania or mania precipitated by antidepressant drugs; bipolar V: depressed patient with bipolar relatives; and bipolar VI: mania without depression) are known to the skilled artisan, and are described in the *Diagnostic and Statistical Manual of Mental Disorders, DSM-IV*, 1994, American Psychiatric Association.

By "schizophrenia" is meant a severe brain disorder characterized by unusual thoughts or perceptions that include hallucinations, delusions, and thought disorder. Other symptoms may include a loss or a decrease in the ability to initiate plans, speak, express emotion, or find pleasure in everyday life. Schizophrenia may include cognitive deficits such as problems with attention, memory, and the ability to plan and organize.

By "nuclear encoded mitochondrial energy metabolism nucleic acid molecule" is meant a polynucleotide, or fragment thereof, that naturally occurs in the nucleus and encodes a polypeptide that localizes to the mitochondria or that functions in mitochondrial energy metabolism.

By "nuclear encoded mitochondrial energy metabolism polypeptide" is meant a protein, or fragment thereof, that functions in mitochondrial energy metabolism and is encoded by a nucleic acid molecule that naturally occurs in the cell nucleus. In some embodiments, the polypeptide functions in oxidative phosphorylation. Specifically excluded by this definition are mitochondrial genome encoded polypeptides.

By "antipsychotic" is meant any pharmaceutical therapy capable of reducing or treating at least one symptom of a psychotic disorder. Antipsychotic include, without limitation, acetophenazine maleate, chlorpromazine hydrochloride, chlorprothixene, chlorprothixene hydrochloride, clozapine, fluphenazine decanoate, fluphenazine enathate, fluphenazine hydrochloride, haloperidol decanoate, haloperidol, haloperidol lactate, lithium carbonate, lithium citrate, loxapine hydrochloride, loxapine succinate, mesoridazine besylate, molindone hydrochloride, perphenazine, pimozide, proclorperazine maleate, proclorperazine, proclorperazine edisylate, promazine hydrochloride, risperidone, thioridazine, thioridazine hydrochloride, thiothixene, thiothixene hydrochloride, and trifluoperazine hydrochloride.

Other features and advantages of the invention will be apparent from the following Detailed Description, the drawings, and the claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A(I) through 1D(IV) show the differential effects on expression of electron transport chain genes in lymphocytes taken from BPD patients as compared to controls cultured under normal and low glucose (stress) conditions. FIGS. 1A(I) through 1A(IV) show probe sets of the electron transport chain with a $p<0.05$ in low glucose BPD over controls (FIG. 1A(I)), normal glucose BPD over controls (FIG. 1A(II)), low over normal glucose controls (FIG. 1A(III)), and low over normal glucose BPD (FIG. 1A(IV)). FIG. 1A(I) shows that seventeen transcripts were downregulated and none were upregulated. FIG. 1A(II) shows that two transcripts (NADH dehydrogenase Fe—S protein 2 and COX VIIa 2 like) were downregulated and three transcripts (NADH dehydrogenase 1 alpha 5, COX IV-1 (213758_at), and COX VIIa 2) were upregulated. FIG. 1A(III) shows eight transcripts were upregulated and none were downregulated. FIG. 1A(IV) shows that six transcripts were downregulated and none were upregulated. Red indicates up-regulation, blue indicates down-regulation, and yellow indicates that no criteria were met. FIGS. 1B(I) through 1B(IV) show comparisons of regulated electron transport transcripts to all regulated transcripts (n=9399 non-redundant probe sets) in low glucose BPD over controls (FIG. 1B(I)), normal glucose BPD over controls (FIG. 1B(II)), low over normal glucose controls (FIG. 1B(III)), and low over normal glucose BPD (FIG. 1B(IV)). Redundant probe sets were masked; transcripts had to be present in at least 50% of all samples. FIGS. 1C(I) through 1C(IV) show that, of all probe sets on the array that were expressed in at least 50% of all samples (n14245), 114 coded for proteins involved in the electron transport chain. Expression levels of each individual probe set were compared between low glucose BPD and low glucose controls (FIG. 1C(I)), normal glucose BPD and normal glucose controls (FIG. 1C(II)), low and normal glucose controls (FIG. 1C(III)) and low and normal glucose BPD ((FIG. 1C(IV)). The solid green line marks equal regulation, the dashed red line shows the actual average regulation of all transcripts. FIGS. 1D(I) through 1D(IV) show real-time Q-rt-PCR analysis for low glucose BPD (n=15) versus controls (n=14; FIG. 1D(I)), high glucose BPD (n=16) versus controls (n=15; FIG. 1D(II)), high glucose versus low glucose controls (FIG. 1D(III)), and high glucose versus low glucose BPD (FIG. 1D(IV)). Four genes were used in the Q-rt-PCR verification: OSCP subunit of ATP synthase (ANOVA: $p=0.006$); ATP synthase subunit c (ANOVA: $p=ns$); ATP synthase subunit g (ANOVA: $p=0.04$); and cytochrome c oxidase IV isoform 1 (ANOVA: $p=0.06$). For each set, the averages of all four genes (ANOVA $p<0.01$) are also shown. Factorial ANOVA5 and Fisher's post hoc protected t-tests; $*p \leq 0.05$; $**p \leq 0.01$.

FIG. 2 is a table showing sample information for BPD and normal control (NC) subjects used to generate the results described above. The following abbreviations are used in FIG. 2: GL (low glucose-gene arrays); GN (normal glucose-gene arrays), PL (low glucose-Q-rt-PCR), PN (normal glucose-Q-rt-PCR), F (fresh lymphocytes); Li (lithium), VA (valproic acid), APD (antipsychotic drugs), AD (antidepressants), AC (anticonvulsants), w (white), a (Asian), m (male), and f (female).

FIG. 3A shows probe sets of the electron transport chain with a p<0.05 in BPD over controls in fresh lymphocytes. One transcript (NADH dehydrogenase 1 beta 7) was upregulated (indicated in red), and the six remaining transcripts were down-regulated (indicated in blue). FIG. 3B shows comparisons of regulated electron transport transcripts to all regulated transcripts (n=9399 non-redundant probe sets); BPD over controls in fresh lymphocytes. Redundant probe sets were masked; transcripts had to be present in at least 50% of all samples. FIG. 3C shows expression levels of the same 114 probe sets shown in FIG. 1, which are compared between BPD and controls in fresh lymphocytes. The Enzo-IVT kit (Enzo Biochem, Farmingdale, N.Y.) was used for biotinylation, which is less efficient than the kits we used for cultured lymphocytes, and thus yielded lower gene expression intensities.

FIG. 6E shows P values of 1-way and factorial analyses (glucose level×treatment); shading indicates that the analysis of variance did not reach significance in both the 1-way and factorial analyses.

DETAILED DESCRIPTION

Figure 3A:
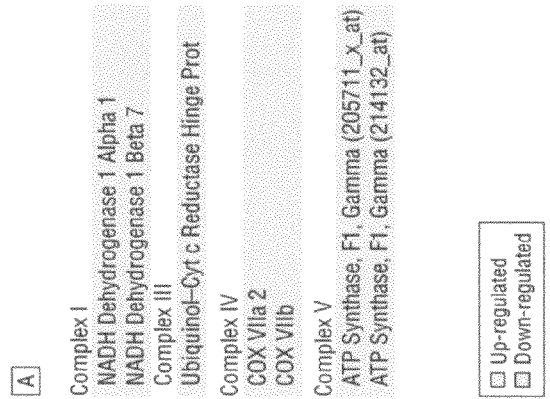
FIGS. 3A-3C show results in fresh, uncultured lymphocytes.

Previous work has identified numerous changes in expression levels of genes in the brains of subjects suffering from bipolar disorder as compared to normal control subjects. While such changes in expression provide a basis for developing diagnostic and prognostic assays for psychotic disorders such as BPD or schizophrenia, one of the challenges in developing a convenient and flexible assay has been identifying whether corresponding expression changes take place in non-neuronal as well as neuronal tissues. As outlined below, we have observed differential gene expression in lymphocytes of individuals diagnosed with BPD as compared to normal controls when the lymphocytes are subjected to stress. In particular, we identified genes involved in mitochondrial function as being differentially regulated in lymphocytes from BPD patients. Based on this discovery, the present invention features diagnostic and prognostic methods that include taking a cell sample from a patient, subjecting the cell from the sample to stress, followed by determining nucleic acid or polypeptide expression in the sample, where an alteration (e.g., a decrease) in expression (e.g., in the nucleic acids or polypeptides identified herein or nucleic acids or polypeptides involved in mitochondrial function) in a cell from the subject as compared to expression in a cell from a control subject indicates that the subject either has or has an increased propensity toward developing a psychotic disorder such as BPD or schizophrenia.

Psychotic Disorders

The diagnostic methods of the invention can be used with any psychotic disorder, including bipolar disorder (BPD) and schizophrenia. Other exemplary psychotic disorders include schizoaffective disorder, schizophreniform disorder, shared psychotic disorder, and brief psychotic disorder. As different psychotic disorders (e.g., BPD and schizophrenia) often share symptoms and a given patient may be diagnosed differently by different physicians or at different institutions, the diagnostic methods of the invention can accordingly be used with any psychotic disorder.

Identification of Differentially Regulated Genes in Psychotic Disorders

Previous work has identified genes differentially regulated in hippocampal tissue taken from deceased subjects with a bipolar disorder or schizophrenia ("diseased subjects"), as compared to tissue taken from deceased subjects free of mental illness ("control subjects") (see U.S. patent application publication 2004/0248286, hereby incorporated by reference). Briefly, RNA from the hippocampal tissue was prepared, and expression levels of transcripts from diseased subjects was compared to that of control subjects. Differential expression of forty-three genes shown in Table 1 below between subjects with bipolar disorder as compared to control subjects were observed.

TABLE 1

Decreased Gene Expression in Bipolar Disorder (p < 0.01)

| | Gene | Map Location | fold | P value | Pres % |
|---|---|---|---|---|---|
| | Mitochondrial | | | | |
| 1 | ATP synthase, mitochondrial F0 complex, subunit c, isoform 3 | 2q31.1 | −1.63 | 0.0006 | 100 |
| 2 | VDAC1 pseudogene, porin protein, isoform 1 | X | −1.41 | 0.0007 | 94 |
| 3 | Ubiquinone-binding protein | 5q31.1 | −1.37 | 0.0011 | 100 |
| 4 | ATP synthase, mitochondrial F0 complex, subunit d | 17q25 | −1.67 | 0.0011 | 100 |
| 5 | Mitochondrial ribosomal protein L3 | 3q21-q23 | −1.46 | 0.0011 | 100 |
| 6 | Cytochrome c oxidase subunit VIIb | Xq13.2 | −1.58 | 0.0013 | 100 |
| 7 | ATP synthase, mitochondrial F0 complex, subunit f, isoform 2 | 7q11.21 | −1.48 | 0.0016 | 100 |
| 8 | Dynamin 1-like | 12p12.1 | −1.66 | 0.0016 | 68 |
| 9 | Voltage-dependent anion channel 2; porin | 10q22 | −1.40 | 0.0018 | 100 |
| 10 | Cytochrome c oxidase subunit VIIa polypeptide 2 (liver) | 6q12 | −1.42 | 0.0021 | 100 |
| 11 | ATP synthase, mitochondrial F1 complex, O subunit (OSCP) | 21q22.11 | −1.53 | 0.0025 | 100 |
| 12 | Voltage-dependent anion channel 1; porin | 5q31 | −1.49 | 0.0029 | 100 |
| 13 | Single-stranded DNA binding protein | 7q34 | −1.44 | 0.0030 | 94 |
| 14 | Fumarate hydratase | 1q42.1 | −1.47 | 0.0036 | 100 |
| 15 | Solute carrier family 25, member 4 | 4q35 | −1.53 | 0.0038 | 100 |
| 16 | ATP synthase, mitochondrial F1 complex, gamma polypeptide 1 | 10q22-q23 | −1.46 | 0.0045 | 100 |
| 17 | NADH dehydrogenase (ubiquinone) 1, alpha/beta subcomplex, 1, 8 kDa | 16p11.2 | −1.45 | 0.0053 | 100 |
| 18 | 3-oxoacid CoA transferase | 5p13 | −1.62 | 0.0089 | 100 |
| | Energy metabolism | | | | |
| 19 | UDP-glucose pyrophosphorylase 2 | 2p14-p13 | −1.44 | 0.0019 | 100 |
| 20 | ATPase, lysosomal 70 kDa, V1 subunit A, isoform 1 | 3q13.31 | −1.54 | 0.0043 | 89 |
| 21 | ATPase, lysosomal 34 kDa, V1 subunit D | 14 | −1.47 | 0.0056 | 100 |
| | Protein degradation | | | | |
| 22 | Sec61 gamma | 7p14.1 | −1.39 | 0.0009 | 100 |
| 23 | Proteasome (prosome, macropain) 26S subunit, ATPase, 6 | 14q22.1 | −1.49 | 0.0021 | 100 |
| 24 | Protein-L-isoaspartate (D-aspartate) O-methyltransferase | 6q24-q25 | −1.75 | 0.0065 | 100 |
| 25 | F-box only protein 9 | 6p12.3-p11.2 | −1.68 | 0.0077 | 100 |
| | Neurotransmission | | | | |
| 26 | Somatostatin | 3q28 | −2.78 | 0.0062 | 84 |
| 27 | Glutamic acid decarboxylase 67 | 2q31 | −1.80 | 0.0090 | 100 |
| | Structural proteins | | | | |
| 28 | Actin related protein 2/3 complex, subunit 3, 21 kDa | 12q24 | −1.49 | 0.0004 | 100 |
| 29 | Beta-tubulin, beta2 | | −1.47 | 0.0019 | 100 |
| 30 | Actin-related protein 2 homolog (yeast) | 2p14 | −1.50 | 0.0022 | 100 |
| | Others | | | | |
| 31 | Macrophage migration inhibitory factor (MIF) | | −1.35 | 0.0007 | 100 |
| 32 | Rho guanine nucleotide exchange factor (GEF) 4 | 2q22 | −1.39 | 0.0012 | 100 |
| 33 | FSHD region gene 1 | 4q35 | −1.42 | 0.0014 | 100 |
| 34 | Eukaryotic translation initiation factor 3 subunit 11 | 19q13.2 | −1.53 | 0.0021 | 100 |
| 35 | Ataxin-10 (spinocerebellar ataxia type 10 protein) | 22q13.31 | −1.67 | 0.0029 | 100 |
| 36 | UDP-GlcNAc:betaGal beta-1,3-N-acetylglucosaminyltransferase 6 | 11q12.1 | −1.50 | 0.0037 | 100 |
| 37 | Contactin 1; glycoprotein gp135 | 12q11-q12 | −1.77 | 0.0046 | 63 |
| 38 | Endosulfine alpha, a regulator of beta-cell K(ATP) channels | 1q21.1 | −1.50 | 0.0048 | 100 |
| 39 | Tyrosine 3-monooxygenase/tryptophan 5-monooxygenase activation protein | 8q23.1 | −1.54 | 0.0067 | 100 |
| 40 | Chromosome 1 open reading frame 15; KIAA0479 protein | 1q25 | −1.67 | 0.0074 | 94 |
| 41 | Arg protein tyrosine kinase binding protein | | −1.51 | 0.0076 | 73 |
| 42 | Fk506-Binding Protein, Alt. Splice 2 | | −1.47 | 0.0078 | 84 |
| 43 | Glutamic-oxaloacetic transaminase 1, soluble (aspartate aminotransferase 1) | 10q24.1-q25.1 | −1.61 | 0.0084 | 100 |

Eighteen of the genes (42%) identified above encode mitochondrial proteins, including subunits of the membrane-bound respiratory enzyme complexes that carry out oxidative phosphorylation in the mitochondrial inner membrane. The changes in gene expression observed in hippocampi from patients with bipolar disorder included a decrease in expression of one gene encoding a component of mitochondrial respiratory complex I, NADH dehydrogenase; a decrease in one gene encoding a component of complex IV, cytochrome c oxidase; and a decrease in five genes encoding components of complex V, ATP synthases.

Functional descriptions of each of the genes in Table 1 are described in Table 2 below.

TABLE 2

Function of Down Regulated Genes ($p < 0.01$)

| Title | Accession No. | Localization | Function |
| --- | --- | --- | --- |
| tyrosine 3-monooxygenase/tryptophan 5-monooxygenase activation protein, zeta polypeptide; Human phospholipase A2 | M86400 | cyoplasmic | activates tyrosine and tryptophan hydroxylases in the presence of ca(2+)/calmodulin-dependent protein kinase ii, and strongly activates protein kinase c. is probably a multifunctional regulator of the cell signaling processes mediated by both kinases. activates the adp-ribosyltransferase (exos) activity of bacterial origin |
| eukaryotic translation initiation factor 3 subunit 11 | AB019392 | | binds to the 40s ribosome and promotes the binding of methionyl-trnai and mrna (by similarity) |
| VDAC1 pseudogene (voltage-dependent anion channel (VDAC) of the outer mitochondrial membrane); porin protein, isoform 1 | AJ002428 | mitochondrial outer membrane | |
| contactin 1; glycoprotein gp135 | Z21488 | peripheral plasma membrane; attached to the membrane by a gpi-anchor | mediates cell surface interactions during nervous system development. in association with cntnap1 seems to play a role in the formation of paranodal axo-glial junctions in myelinated peripheral nerves and may have a role in the signaling between axons and myelinating glial cells |
| chromosome 1 open reading frame 15; KIAA0479 protein; nicotinamide mononucleotide adenylyltransferase 2 | AB007948 | cytoplasmic | This gene product belongs to the nicotinamide mononucleotide adenylyltransferase (NMNAT) enzyme family, members of which catalyze an essential step in NAD (NADP) biosynthetic pathway. |
| fumarate hydratase | U59309 | mitochondrial | tricarboxylic acid cycle |
| solute carrier family 25 (mitochondrial carrier; adenine nucleotide translocator), member 4 | J02966 | mitochondrial inner membrane | catalyzes the exchange of adp and atp across the mitochondrial inner membrane |
| UDP-GlcNAc:betaGal beta-1,3-N-acetylglucosaminyltransferase 6; i-beta-1,3-N-acetylglucosaminyltransferase | AF029893 | type ii membrane protein. golgi. | can initiate the synthesis or the elongation of the linear poly-n-acetyllactosaminoglycans |
| *Homo sapiens* beta 2; beta-tubulin | X02344 | | |
| ATPase, H+ transporting, lysosomal 34 kDa, V1 subunit D | AA877795 | lysosomal | vacuolar ATPase (V-ATPase), a multisubunit enzyme that mediates acidification of eukaryotic intracellular organelles. |
| low molecular mass ubiquinone-binding protein (9.5 kD); ubiquinol-cytochrome c reductase complex ubiquinone-binding protein | AI540957 | mitochondrial inner membrane | component of the ubiquinol-cytochrome c reductase complex (complex iii or cytochrome b-c1 complex), |
| ATP synthase, H+ transporting, mitochondrial F0 complex, subunit c (subunit 9) isoform 3 | U09813 | mitochondrial inner membrane | ATP synthase, H+ transporting |
| ATPase, H+ transporting, lysosomal 70 kDa, V1 subunit A, isoform 1 | L09235 | vacuolar | catalytic subunit of the peripheral v1 complex of vacuolar atpase. v-atpase vacuolar atpase is responsible for acidifying a variety of intracellular compartments in eukaryotic cells |
| NADH dehydrogenase (ubiquinone) 1, alpha/beta subcomplex, 1, 8 kDa | AC002400 | mitochondrial inner membrane | complex i is composed of about 30 different subunits |
| glutamic-oxaloacetic transaminase 1, soluble (aspartate aminotransferase 1) | M37400 | cyoplasmic | l-aspartate + 2-oxoglutarate = oxaloacetate + l-glutamate |
| ARP2 actin-related protein 2 homolog (yeast); one of seven subunits of the Arp2/3 protein complex; actin-related protein. | AF006082 | cytoskeleton | part of a complex implicated in the control of actin polymerization in cells |
| ATP synthase, H+ transporting, mitochondrial F0 complex, subunit d | AF087135 | mitochondrial inner membrane | this is one of the chains of the nonenzymatic component (cf(0) subunit) of the mitochondrial atpase complex. |

TABLE 2-continued

Function of Down Regulated Genes (p < 0.01)

| Title | Accession No. | Localization | Function |
|---|---|---|---|
| actin related protein 2/3 complex, subunit 3, 21 kDa | AI525393 | cytoplasmic | part of a complex implicated in the control of actin polymerization in cells |
| Identification of ArgBP1, an Arg protein tyrosine kinase binding protein that is the human homologue of a CNS-specific Xenopus gene | X95677 | cytoskeleton | Arg protein tyrosine kinase binding protein |
| Rho guanine nucleotide exchange factor (GEF) 4 | AB029035 | | |
| cytochrome c oxidase subunit VIIb | N50520 | mitochondrial inner membrane | |
| ATP synthase, H+ transporting, mitochondrial F1 complex, O subunit (oligomycin sensitivity conferring protein) | X83218 | mitochondrial inner membrane | |
| glutamate decarboxylase 1 (brain, 67 kDa) | M81883 | | |
| UDP-glucose pyrophosphorylase 2 | U27460 | cyoplasmic | plays a central role as a glucosyl donor in cellular metabolic pathways |
| voltage-dependent anion channel 2; porin, mitochondrial | L08666 | mitochondrial outer membrane | forms a channel through the mitochondrial outer membrane that allows diffusion of small hydrophilic molecules. the channel adopts an open conformation at low or zero membrane potential and a closed conformation at potentials above 30-40 mv. the open state has a weak anion selectivity whereas the closed state is cation-selective |
| mitochondrial ribosomal protein L3 | X06323 | mitochondrial | belongs to the l3p family of ribosomal proteins |
| protein-L-isoaspartate (D-aspartate) O-methyltransferase | D25547 | cyoplasmic | catalyzes the methyl esterification of l-isoaspartyl and d-aspartyl residues in peptides and proteins that result from spontaneous decomposition of normal l-aspartyl and l-asparaginyl residues. it plays a role in the repair and/or degradation of damaged proteins |
| somatostatin | J00306 | secreted | somatostatin inhibits the release of somatotropin |
| single-stranded DNA binding protein | AA768912 | mitochondrial | this protein binds preferentially and cooperatively to ss-dna. probably involved in mitochondrial dna replication |
| FSHD region gene 1 | L76159 | | deleted in facioscapulohumeral muscular dystrophy |
| F-box only protein 9 | AL031178 | | probably recognizes and binds to some phosphorylated proteins and promotes their ubiquitination and degradation; The F-box proteins constitute one of the four subunits of the ubiquitin protein ligase complex called SCFs |
| endosulfine alpha, a regulator of beta-cell K(ATP) channels | X99906 | | endogenous ligand for sulfonylurea receptor. by inhibiting sulfonylurea from binding to the receptor, it reduces k(atp) channel currents and thereby stimulates insulin secretion |
| Sec61 gamma; necessary for protein translocation in the endoplasmic reticulum | AF054184 | ER | necessary for protein translocation in the endoplasmic reticulum |
| like mouse brain protein E46; ataxin-10 (spinocerebellar ataxia type 10 protein) | AL050282 | | defects in sca10 are the cause of spinocerebellar ataxia type 10 |
| ATP synthase, H+ transporting, mitochondrial F1 complex, gamma polypeptide 1 | D16562 | mitochondrial inner membrane | |
| ATP synthase, H+ transporting, mitochondrial F0 complex, subunit f, isoform 2 | AF047436 | mitochondrial inner membrane | |
| voltage-dependent anion channel 1; Outer membrane; Porin; Mitochondrion | L06132 | mitochondrial outer membrane | Porin; |
| 3-oxoacid CoA transferase; Mitochondrion; Transferase | U62961 | mitochondrial matrix | key enzyme for ketone body catabolism. transfers the coa moiety from succinate to acetoacetate. formation of the enzyme-coa intermediate proceeds via an unstable anhydride species formed between the carboxylate groups of the enzyme and substrate |
| dynamin 1-like; This protein establishes mitochondrial morphology through a role in distributing mitochondrial tubules throughout the cytoplasm. | AF000430 | mitochondrial matrix Cytoplasm | This protein establishes mitochondrial morphology through a role in distributing mitochondrial tubules throughout the cytoplasm. |
| cytochrome c oxidase subunit VIIa polypeptide 2 (liver) | NM_001865 | mitochondrial inner membrane | complex IV |
| macrophage migration inhibitory factor (MIF) | L19686 | | |

TABLE 2-continued

Function of Down Regulated Genes (p < 0.01)

| Title | Accession No. | Localization | Function |
|---|---|---|---|
| proteasome (prosome, macropain) 26S subunit, ATPase, 6 | D78275 | cytoplasmic and nuclear | involved in the atp-dependent degradation of ubiquitinated proteins |
| Fk506-Binding Protein, Alt. Splice 2 | X52220 | | |

Using a different statistical threshold (p<0.02), an additional two hundred sixty three genes were identified that are differentially expressed in patients having a bipolar disorder.

Table 3 provides an inclusive list of the three hundred six genes identified as regulated in patients having bipolar disorder (p level<0.02; fold induction>1.2), their Genebank accession numbers, fold change, and p value.

TABLE 4

Function of Differentially Expressed Genes (p < 0.02)

| Gene Description | Accession # | Fold Change | P value |
|---|---|---|---|
| thymosin, beta 10 | M92383 | −1.31 | 0.01063 |
| Cluster Incl. S81916: phosphoglycerate kinase {alternatively spliced} [human, phosphoglycerate kinase deficient patient with episodes of muscl, mRNA Partial Mutant, 307 nt] /cds = (0, 143)//ug = Hs.169313 /len = 307 | S81916 | −1.46 | 0.019787 |
| muscle specific gene | AB019392 | −1.53 | 0.002077 |
| reticulon 4 | AB020693 | −1.28 | 0.013635 |
| voltage-dependent anion channel 1 pseudogene | AJ002428 | −1.41 | 0.000727 |
| p21 (CDKN1A)-activated kinase 3 | AF068864 | −1.53 | 0.016696 |
| p21 (CDKN1A)-activated kinase 3 | AF068864 | −1.55 | 0.014761 |
| similar to S. pombe dim1+ | AF023612 | −1.23 | 0.006959 |
| guanine nucleotide binding protein (G protein), alpha 13 | L22075 | 1.49 | 0.018088 |
| tubulin, beta, 2 | X02344 | −1.47 | 0.001895 |
| tubulin, beta, 2 | X02344 | −1.41 | 0.003694 |
| D-dopachrome tautomerase | AF012434 | −1.23 | 0.013399 |
| Cluster Incl. AL050065: Homo sapiens mRNA; cDNA DKFZp566M043 (from clone DKFZp566M043) /cds = UNKNOWN /gb = AL050065 /gi = 4884295 /ug = Hs.212587 /len = 1568 | AL050065 | 1.27 | 0.000158 |
| keratin, hair, acidic, 3B | X82634 | 1.24 | 0.012361 |
| tyrosine 3-monooxygenase/tryptophan 5-monooxygenase activation protein, zeta polypeptide | U28964 | −1.39 | 0.007862 |
| ribosomal protein S7 | Z25749 | −1.22 | 0.017676 |
| KIAA0316 gene product | AB002314 | −1.37 | 0.013021 |
| fibroblast growth factor 9 (glia-activating factor) | D14838 | −1.29 | 0.014416 |
| Cluster Incl. X95677: H. sapiens mRNA for ArgBPIB protein /cds = (134, 1033) /gb = X95677 /gi = 1491701 /ug = Hs.169237 /len = 2374 | X95677 | −1.5 | 0.004338 |
| KIAA1032 protein | AB028955 | −1.45 | 0.004604 |
| tyrosine 3-monooxygenase/tryptophan 5-monooxygenase activation protein, beta polypeptide | X57346 | −1.34 | 0.016325 |
| pyruvate kinase, muscle | M26252 | −1.22 | 0.012184 |
| dentatorubral-pallidoluysian atrophy (atrophin-1) | U47924 | −1.34 | 0.005434 |
| DNA segment on chromosome 6(unique) 2654 expressed sequence | Y18504 | −1.21 | 0.016847 |
| EGF-like-domain, multiple 4 | AB011541 | −1.3 | 0.008183 |
| acylphosphatase 2, muscle type | X84195 | −1.34 | 0.004579 |
| tachykinin, precursor 1 (substance K, substance P, neurokinin 1, neurokinin 2, neuromedin L, neurokinin alpha, neuropeptide K, neuropeptide gamma) | U37529 | −3.12 | 0.011804 |
| ribosomal protein L10a | AL022721 | −1.28 | 0.017343 |
| gamma-aminobutyric acid (GABA) A receptor, alpha 2 | S62907 | −1.4 | 0.007998 |
| potassium inwardly-rectifying channel, subfamily J, member 6 | U52153 | −1.37 | 0.018175 |
| GNAS complex locus | X04409 | −1.23 | 0.015949 |
| GNAS complex locus | X04409 | −1.28 | 0.004268 |
| somatostatin | AI636761 | −2.74 | 0.006587 |
| RAD51-like 3 (S. cerevisiae) | AF034956 | 1.32 | 0.011514 |
| guanine nucleotide binding protein (G protein), beta 5 | AF017656 | −1.36 | 0.007348 |
| KIAA0377 gene product | AB002375 | −1.22 | 0.014708 |
| ribonuclease H1 | AF039652 | −1.28 | 0.008304 |
| neuropeptide Y | AI198311 | −1.84 | 0.017551 |
| NADH dehydrogenase (ubiquinone) 1 beta subcomplex, 1 (7 kD, MNLL) | AI345944 | −1.39 | 0.004675 |
| FSHD region gene 1 | L76159 | −1.42 | 0.001405 |
| Cluster Incl. AA780435: ae93d06.s1 Homo sapiens cDNA, 3 end /clone = 1020491 /clone_end = 3 /gb = AA780435 /gi = 2839766 /ug = Hs.204446 /len = 451 | AA780435 | 1.25 | 0.015387 |
| T-box, brain, 1 | U49250 | 1.24 | 0.014785 |
| desmocollin 2 | X56807 | 1.22 | 0.005732 |
| amyloid beta (A4) precursor protein-binding, family A, member 2 (X11-like) | AF047348 | −1.32 | 0.007039 |
| Cluster Incl. AL050204: Homo sapiens mRNA; cDNA DKFZp586F1223 (from clone DKFZp586F1223) /cds = UNKNOWN /gb = AL050204 /gi = 4884443 /ug = Hs.28540 /len = 1634 | AL050204 | 1.24 | 0.015298 |

TABLE 4-continued

Function of Differentially Expressed Genes (p < 0.02)

| Gene Description | Accession # | Fold Change | P value |
| --- | --- | --- | --- |
| chloride intracellular channel 2 | Y12696 | 1.21 | 0.003863 |
| chemokine (C-X3-C) receptor 1 | U20350 | −2.42 | 0.017113 |
| Cluster Incl. AI659108: tu08c09.x1 Homo sapiens cDNA, 3 end /clone = IMAGE-2250448 /clone__end = 3 /gb = AI659108 /gi = 4762678 /ug = Hs.99093 /len = 492 | AI659108 | −1.28 | 0.016605 |
| DKFZP566B183 protein | AL050272 | −1.58 | 0.019681 |
| v-myb myeloblastosis viral oncogene homolog (avian) | M13666 | 1.23 | 0.004209 |
| contactin 1 | Z21488 | −1.79 | 0.004286 |
| chromosome 1 open reading frame 15 | AB007948 | −1.79 | 0.006118 |
| sortilin-related receptor, L(DLR class) A repeats-containing | Y08110 | −1.34 | 0.010094 |
| down-regulator of transcription 1, TBP-binding (negative cofactor 2) | M97388 | −1.24 | 0.003746 |
| vesicle-associated soluble NSF attachment protein receptor (v-SNARE; homolog of S. cerevisiae VTI1) | AF060902 | −1.28 | 0.003184 |
| neuronal protein | W28770 | −1.66 | 0.011113 |
| putatative 28 kDa protein | L48692 | −1.36 | 0.019003 |
| Cluster Incl. AL109702: Homo sapiens mRNA full length insert cDNA clone EUROIMAGE 42138 /cds = UNKNOWN /gb = AL109702 /gi = 5689811 /ug = Hs.19720 /len = 1869 | AL109702 | −1.23 | 0.007009 |
| ubiquitin-conjugating enzyme E2M (UBC12 homolog, yeast) | AF075599 | −1.22 | 0.001561 |
| kinesin family member 3B | AB002357 | −1.32 | 0.006715 |
| eukaryotic translation elongation factor 1 alpha 2 | X70940 | −1.34 | 0.015877 |
| RNA 3'-terminal phosphate cyclase | Y11651 | −1.28 | 0.01692 |
| proline-rich Gla (G-carboxyglutamic acid) polypeptide 1 | AF009242 | 1.22 | 0.019808 |
| necdin homolog (mouse) | U35139 | −1.41 | 0.014012 |
| src family associated phosphoprotein 2 | AF051323 | −1.37 | 0.006528 |
| excision repair cross-complementing rodent repair deficiency, complementation group 1 (includes overlapping antisense sequence) | M13194 | −1.21 | 0.003425 |
| Rho guanine nucleotide exchange factor (GEF) 4 | AB029035 | −1.39 | 0.001221 |
| U6 snRNA-associated Sm-like protein LSm7 | AA121509 | −1.32 | 0.010447 |
| glutamate decarboxylase 1 (brain, 67 kD) | M81883 | −1.84 | 0.008965 |
| paraneoplastic antigen MA2 | AB020690 | −1.39 | 0.018583 |
| programmed cell death 6 | AF035606 | −1.33 | 0.004502 |
| cytoplasmic FMRP interacting protein 2 | L47738 | −1.22 | 0.01979 |
| ATP synthase, H+ transporting, mitochondrial F1 complex, delta subunit | AI436567 | −1.27 | 0.002319 |
| transcription elongation factor A (SII)-like 1 | M99701 | −1.2 | 0.016432 |
| Cluster Incl. AL049321: Homo sapiens mRNA; cDNA DKFZp564D156 (from clone DKFZp564D156) /cds = UNKNOWN /gb = AL049321 /gi = 4500094 /ug = Hs.9927 /len = 1440 | AL049321 | 1.27 | 0.019168 |
| NADH dehydrogenase (ubiquinone) Fe—S protein 4 (18 kD) (NADH-coenzyme Q reductase) | AA203303 | −1.42 | 0.009172 |
| chromosome 14 open reading frame 2 | AF054175 | −1.32 | 0.002134 |
| NADH dehydrogenase (ubiquinone) 1 beta subcomplex, 3 (12 kD, B12) | AA203354 | −1.36 | 0.008742 |
| Cluster Incl. AL031178: Human DNA sequence from clone 341E18 on chromosome 6p11.2-12.3. Contains a Serine/Threonine Protein Kinase gene (presumptive isolog of a Rat gene) and a novel alternatively spliced gene. Contains a putative CpG island, ESTs and GSSs | AL031178 | −1.68 | 0.007684 |
| Cluster Incl. N98670: yy66d08.r1 Homo sapiens cDNA, 5 end /clone = IMAGE-278511 /clone__end = 5 /gb = N98670 /gi = 1270092 /ug = Hs.111632 /len = 574 | N98670 | −1.27 | 0.008167 |
| endosulfine alpha | AI658639 | −1.3 | 0.010107 |
| endosulfine alpha | X99906 | −1.55 | 0.001717 |
| microsomal glutathione S-transferase 3 | AF026977 | −1.39 | 0.001451 |
| proteasome (prosome, macropain) subunit, beta type, 7 | D38048 | −1.28 | 0.004323 |
| non-metastatic cells 1, protein (NM23A) expressed in | AL038662 | −1.65 | 0.008898 |
| DR1-associated protein 1 (negative cofactor 2 alpha) | AI991040 | −1.28 | 0.002766 |
| ADP-ribosylation factor 3 | M74491 | −1.21 | 0.012197 |
| methionine-tRNA synthetase | X94754 | −1.2 | 0.004773 |
| HMT1 hnRNP methyltransferase-like 1 (S. cerevisiae) | X99209 | −1.21 | 0.018481 |
| glypican 3 | U50410 | 1.23 | 0.005816 |
| putative breast adenocarcinoma marker (32 kD) | AF042384 | −1.21 | 0.009768 |
| KIAA0935 protein | AB023152 | −1.24 | 0.009612 |
| microtubule-associated proteins 1A/1B light chain 3 | W28807 | −1.27 | 0.002703 |
| cytochrome c oxidase subunit Vb | M19961 | −1.29 | 0.003535 |
| like mouse brain protein E46 | AL050282 | −1.67 | 0.002917 |
| P311 protein | U30521 | −1.3 | 0.017844 |
| nuclear receptor co-repressor 1 | AF044209 | −1.21 | 0.010503 |
| cullin 1 | U58087 | −1.31 | 0.002505 |
| peroxiredoxin 2 | L19185 | −1.31 | 0.007342 |
| nascent-polypeptide-associated complex alpha polypeptide | AF054187 | −1.24 | 0.013613 |
| polymerase (RNA) II (DNA directed) polypeptide B (140 kD) | X63563 | −1.3 | 0.005797 |
| proteasome (prosome, macropain) 26S subunit, non-ATPase, 4 | U51007 | −1.22 | 0.010387 |
| protein phosphatase 3 (formerly 2B), catalytic subunit, beta isoform (calcineurin A beta) | M29551 | −1.45 | 0.013912 |
| ATPase, Ca++ transporting, cardiac muscle, slow twitch 2 | M23115 | −1.4 | 0.011465 |
| KIAA0090 protein | D42044 | 1.21 | 0.01314 |
| ATP synthase, H+ transporting, mitochondrial F1 complex, alpha subunit, isoform 1, cardiac muscle | D14710 | −1.38 | 0.001708 |

TABLE 4-continued

Function of Differentially Expressed Genes (p < 0.02)

| Gene Description | Accession # | Fold Change | P value |
|---|---|---|---|
| aldolase C, fructose-bisphosphate | AF054987 | −1.29 | 0.01524 |
| isocitrate dehydrogenase 3 (NAD+) beta | AA552698 | −1.26 | 0.004632 |
| ATP synthase, H+ transporting, mitochondrial F1 complex, gamma polypeptide 1 | D16562 | −1.46 | 0.004519 |
| ATP synthase, H+ transporting, mitochondrial F0 complex, subunit f, isoform 2 | AF047436 | −1.48 | 0.001591 |
| dynactin 3 (p22) | W26651 | −1.25 | 0.014741 |
| solute carrier family 25 (mitochondrial carrier; adenine nucleotide translocator), member 6 | J03592 | −1.28 | 0.008112 |
| transcriptional activator of the c-fos promoter | D54318 | −1.41 | 0.004007 |
| transcriptional activator of the c-fos promoter | U49857 | −1.36 | 0.013221 |
| serologically defined breast cancer antigen 84 | AF091085 | −1.24 | 0.004593 |
| glutamic-oxaloacetic transaminase 2, mitochondrial (aspartate aminotransferase 2) | M22632 | −1.26 | 0.019781 |
| RNA binding motif protein 8A | AL049219 | −1.22 | 0.00522 |
| isoleucine-tRNA synthetase | U04953 | −1.32 | 0.01167 |
| cytochrome c oxidase subunit VIb | T57872 | −1.29 | 0.005962 |
| glycogenin | U31525 | −1.25 | 0.019465 |
| melanoma antigen, family D, 1 | W26633 | −1.41 | 0.005774 |
| 3-oxoacid CoA transferase | U62961 | −1.62 | 0.008802 |
| dynamin 1-like | AF000430 | −1.66 | 0.001584 |
| phosphoglycerate mutase 1 (brain) | J04173 | −1.23 | 0.013865 |
| cytochrome c oxidase subunit Va | M22760 | −1.4 | 0.00763 |
| leucine-rich PPR-motif containing | M92439 | −1.31 | 0.015861 |
| cytochrome c oxidase subunit VIIa polypeptide 2 (liver) | AA978033 | −1.42 | 0.00198 |
| ATX1 antioxidant protein 1 homolog (yeast) | U70660 | −1.23 | 0.009151 |
| v-Ki-ras2 Kirsten rat sarcoma 2 viral oncogene homolog | L00049 | −1.36 | 0.006442 |
| eukaryotic translation initiation factor 3, subunit 2 (beta, 36 kD) | U39067 | −1.21 | 0.014181 |
| NADH dehydrogenase (ubiquinone) 1 beta subcomplex, 8 (19 kD, ASHI) | AI541050 | −1.22 | 0.011804 |
| solute carrier family 25 (mitochondrial carrier; adenine nucleotide translocator), member 4 | J02966 | −1.53 | 0.003831 |
| translocase of inner mitochondrial membrane 17 homolog A (yeast) | X97544 | −1.26 | 0.001239 |
| chromogranin B (secretogranin 1) | Y00064 | −2.09 | 0.011271 |
| lactate dehydrogenase B | X13794 | −1.21 | 0.003571 |
| ATPase, H+ transporting lysosomal (vacuolar proton pump), member M | AA877795 | −1.35 | 0.009456 |
| glutathione peroxidase 4 (phospholipid hydroperoxidase) | X71973 | −1.23 | 0.013006 |
| low molecular mass ubiquinone-binding protein (9.5 kD) | AI540957 | −1.37 | 0.00106 |
| palmitoyl-protein thioesterase 1 (ceroid-lipofuscinosis, neuronal 1, infantile) | U44772 | −1.39 | 0.00881 |
| nardilysin (N-arginine dibasic convertase) | X93209 | −1.21 | 0.011077 |
| ATP synthase, H+ transporting, mitochondrial F0 complex, subunit c (subunit 9) isoform 3 | U09813 | −1.63 | 0.000557 |
| ceroid-lipofuscinosis, neuronal 3, juvenile (Batten, Spielmeyer-Vogt disease) | AC002544 | −1.24 | 0.006393 |
| CGI-51 protein | AL035398 | −1.26 | 0.001213 |
| seryl-tRNA synthetase | X91257 | −1.4 | 0.008777 |
| melanoma antigen, family D, 2 | Z98046 | −1.23 | 0.007847 |
| ATPase, H+ transporting, lysosomal (vacuolar proton pump), alpha polypeptide, 70 kD, isoform 1 | L09235 | −1.54 | 0.00433 |
| NADH dehydrogenase (ubiquinone) Fe—S protein 3 (30 kD) (NADH-coenzyme Q reductase) | AF067139 | −1.34 | 0.001686 |
| golgi associated, gamma adaptin ear containing, ARF binding protein 2 | AC002400 | −1.45 | 0.005359 |
| GDP dissociation inhibitor 2 | Y13286 | −1.31 | 0.01581 |
| Ras-related GTP-binding protein | U41654 | −1.39 | 0.009322 |
| meningioma expressed antigen 5 (hyaluronidase) | AB014579 | −1.26 | 0.011112 |
| Cluster Incl. AF055023: Homo sapiens clone 24723 mRNA sequence /cds = UNKNOWN /gb = AF055023 /gi = 3005751 /ug = Hs.58220 /len = 1834 | AF055023 | 1.26 | 0.004067 |
| glutamic-oxaloacetic transaminase 1, soluble (aspartate aminotransferase 1) | M37400 | −1.61 | 0.008363 |
| COP9 (constitutive photomorphogenic, Arabidopsis, homolog) subunit 3 | AF031647 | −1.26 | 0.009059 |
| ribosomal protein L3 | AL022326 | −1.38 | 0.010345 |
| amyloid beta precursor protein binding protein 1, 59 kD | U50939 | −1.26 | 0.005884 |
| ARP2 actin-related protein 2 homolog (yeast) | AF006082 | −1.5 | 0.002224 |
| succinate dehydrogenase complex, subunit B, iron sulfur (Ip) | U17886 | −1.23 | 0.005271 |
| ATP synthase, H+ transporting, mitochondrial F0 complex, subunit d | AF087135 | −1.67 | 0.001078 |
| Cluster Incl. AA527880: nh86h10.s1 Homo sapiens cDNA, 3 end /clone = IMAGE-965443 /clone_end = 3 /gb = AA527880 /gi = 2269949 /ug = Hs.661 /len = 568 | AA527880 | −1.23 | 0.011144 |
| actin related protein 2/3 complex, subunit 3 (21 kD) | AI525393 | −1.49 | 0.000404 |
| polymerase (RNA) II (DNA directed) polypeptide L (7.6 kD) | N24355 | −1.24 | 0.000766 |
| voltage-dependent anion channel 3 | AF038962 | −1.3 | 0.009254 |
| ubiquinol-cytochrome c reductase hinge protein | AA526497 | −1.37 | 0.002659 |
| ATP synthase, H+ transporting, mitochondrial F0 complex, subunit F6 | AA845575 | −1.39 | 0.003637 |
| proteasome (prosome, macropain) subunit, alpha type, 6 | X59417 | −1.37 | 0.003532 |
| dynactin 1 (p150, glued homolog, Drosophila) | AF086947 | −1.23 | 0.016308 |
| protein tyrosine phosphatase, receptor type, N polypeptide 2 | U81561 | −1.41 | 0.019536 |
| cytochrome c oxidase subunit VIc | W51774 | −1.43 | 0.003852 |
| NADH dehydrogenase (ubiquinone) 1 alpha subcomplex, 1 (7.5 kD, MWFE) | N47307 | −1.34 | 0.004606 |
| tubulin-specific chaperone c | U61234 | −1.24 | 0.003964 |
| low density lipoprotein-related protein-associated protein 1 (alpha-2-macroglobulin receptor-associated protein 1) | M63959 | −1.2 | 0.013075 |
| glyoxalase I | D13315 | −1.32 | 0.012924 |
| glycyl-tRNA synthetase | U09510 | −1.27 | 0.012995 |

TABLE 4-continued

Function of Differentially Expressed Genes (p < 0.02)

| Gene Description | Accession # | Fold Change | P value |
|---|---|---|---|
| glycyl-tRNA synthetase | U09510 | −1.32 | 0.011219 |
| aldo-keto reductase family 1, member B1 (aldose reductase) | X15414 | −1.35 | 0.004964 |
| nucleolar and coiled-body phosphprotein 1 | D21262 | −1.24 | 0.002917 |
| cytochrome c oxidase subunit VIIb | N50520 | −1.56 | 0.001375 |
| coatomer protein complex, subunit alpha | U24105 | −1.32 | 0.01774 |
| ATP synthase, H+ transporting, mitochondrial F1 complex, O subunit (oligomycin sensitivity conferring protein) | X83218 | −1.48 | 0.001619 |
| dynein, cytoplasmic, heavy polypeptide 1 | AB002323 | −1.28 | 0.012195 |
| uncharacterized bone marrow protein BM036 | AI057607 | −1.26 | 0.005077 |
| farnesyl diphosphate synthase (farnesyl pyrophosphate synthetase, dimethylallyltranstransferase, geranyltranstransferase) | D14697 | −1.32 | 0.016932 |
| NADH dehydrogenase (ubiquinone) flavoprotein 1 (51 kD) | AF053070 | −1.25 | 0.012356 |
| ATPase, H+ transporting, lysosomal (vacuolar proton pump) 31 kD | X76228 | −1.4 | 0.010499 |
| UDP-glucose pyrophosphorylase 2 | U27460 | −1.44 | 0.001884 |
| ATPase, vacuolar, 14 kD | D49400 | −1.27 | 0.001322 |
| inner membrane protein, mitochondrial (mitofilin) | L42572 | −1.22 | 0.017318 |
| DEAD/H (Asp-Glu-Ala-Asp/His) box polypeptide 1 | X70649 | −1.37 | 0.005672 |
| uroporphyrinogen decarboxylase | AF104421 | −1.29 | 0.005848 |
| complement component 1, q subcomponent binding protein | M69039 | −1.33 | 0.00363 |
| solute carrier family 25 (mitochondrial carrier; phosphate carrier), member 3 | X60036 | −1.35 | 0.008737 |
| Cluster Incl. L08666: Homo sapiens porin (por) mRNA, complete cds and truncated cds /cds = UNKNOWN /gb = L08666 /gi = 190199 /ug = Hs.78902 /len = 1464 | L08666 | −1.35 | 0.010491 |
| mitochondrial ribosomal protein L3 | X06323 | −1.43 | 0.000177 |
| protein-L-isoaspartate (D-aspartate) O-methyltransferase | D25547 | −1.75 | 0.006481 |
| proteasome (prosome, macropain) 26S subunit, ATPase, 5 | AF035309 | −1.23 | 0.010559 |
| IK cytokine, down-regulator of HLA II | AJ005579 | −1.25 | 0.00818 |
| hepatitis B virus x-interacting protein (9.6 kD) | AF029890 | −1.3 | 0.009123 |
| NADH dehydrogenase (ubiquinone) Fe—S protein 5 (15 kD) (NADH-coenzyme Q reductase) | AI541336 | −1.27 | 0.012446 |
| ATP synthase, H+ transporting, mitochondrial F0 complex, subunit c (subunit 9), isoform 1 | X69907 | −1.28 | 0.004027 |
| cytochrome c oxidase subunit VIII | AI525665 | −1.22 | 0.003607 |
| chromobox homolog 3 (HP1 gamma homolog, Drosophila) | AI740522 | −1.26 | 0.003802 |
| proteasome (prosome, macropain) subunit, alpha type, 1 | M64992 | −1.31 | 0.017706 |
| Cluster Incl. U66042: Human clone 191B7 placenta expressed mRNA from chromosome X /cds = UNKNOWN /gb = U66042 /gi = 1519267 /ug = Hs.82171 /len = 1327 | U66042 | −1.2 | 0.002954 |
| glutathione synthetase | U34683 | −1.23 | 0.014357 |
| peroxiredoxin 4 | U25182 | −1.28 | 0.014485 |
| Sjogren syndrome antigen B (autoantigen La) | X69804 | −1.22 | 0.01958 |
| hypothetical protein MGC10715 | AL049650 | −1.22 | 0.016112 |
| peptidylglycine alpha-amidating monooxygenase | M37721 | −1.39 | 0.016292 |
| dynactin 2 (p50) | U50733 | −1.23 | 0.013766 |
| single-stranded DNA-binding protein 1 | AA768912 | −1.42 | 0.003143 |
| single-stranded DNA-binding protein 1 | AA768912 | −1.3 | 0.014364 |
| eukaryotic translation initiation factor 4B | X55733 | −1.2 | 0.014218 |
| GCN5 general control of amino-acid synthesis 5-like 1 (yeast) | AI525379 | −1.37 | 0.001552 |
| nitrogen fixation cluster-like | U47101 | −1.29 | 0.018877 |
| Sec61 gamma | AF054184 | −1.39 | 0.000911 |
| transcription elongation factor B (SIII), polypeptide 2 (18 kD, elongin B) | AI857469 | −1.25 | 0.004063 |
| ectonucleoside triphosphate diphosphohydrolase 6 (putative function) | AL035252 | −1.24 | 0.00585 |
| cutaneous T-cell lymphoma-associated tumor antigen se20-4; differentially expressed nucleolar TGF-beta1 target protein (DENTT) | AB015345 | −1.28 | 0.010929 |
| SET translocation (myeloid leukemia-associated) | M93651 | −1.27 | 0.007058 |
| voltage-dependent anion channel 1 | L06132 | −1.49 | 0.00374 |
| NADH dehydrogenase (ubiquinone) 1 alpha subcomplex, 2 (8 kD, B8) | AF047185 | −1.27 | 0.002062 |
| eukaryotic translation elongation factor 1 epsilon 1 | AF054186 | −1.33 | 0.017208 |
| hypothetical protein | H15872 | −1.27 | 0.011372 |
| Cluster Incl. AI382123: te30a09.x1 Homo sapiens cDNA, 3 end /clone = IMAGE-2087416 /clone_end = 3 /gb = AI382123 /gi = 4194904 /ug = Hs.182919 /len = 857 | AI382123 | −1.43 | 0.01227 |
| SWI/SNF related, matrix associated, actin dependent regulator of chromatin, subfamily a, member 2 | D26155 | −1.36 | 0.002574 |
| KIAA0447 gene product | AB007916 | −1.22 | 0.018871 |
| JTV1 gene | U24169 | −1.23 | 0.01197 |
| thyroid hormone receptor interactor 3 | L40410 | −1.31 | 0.007183 |
| KIAA1049 protein | AB028972 | −1.37 | 0.003695 |
| integral membrane protein 2B | AA477898 | −1.32 | 0.008173 |
| lactate dehydrogenase A | X02152 | −1.37 | 0.009983 |
| protein phosphatase 1, regulatory subunit 7 | Z50749 | −1.36 | 0.001411 |
| adaptor-related protein complex 1, sigma 2 subunit | AF091077 | −1.38 | 0.015644 |
| Cluster Incl. AA203545: zx59a05.r1 Homo sapiens cDNA, 5 end /clone = IMAGE-446768 /clone_end = 5 /gb = AA203545 /gi = 1799271 /ug = Hs.56876 /len = 568 | AA203545 | −1.29 | 0.018083 |
| emopamil binding protein (sterol isomerase) | Z37986 | −1.2 | 0.013307 |
| fumarate hydratase | U59309 | −1.47 | 0.003497 |
| protein translocation complex beta | AA083129 | −1.21 | 0.009925 |
| proteasome (prosome, macropain) 26S subunit, non-ATPase, 8 | D38047 | −1.3 | 0.014744 |
| regulator of G-protein signalling 10 | AF045229 | −1.3 | 0.002964 |

TABLE 4-continued

Function of Differentially Expressed Genes (p < 0.02)

| Gene Description | Accession # | Fold Change | P value |
|---|---|---|---|
| UDP-GlcNAc: betaGal beta-1,3-N-acetylglucosaminyltransferase 6 | AF029893 | −1.5 | 0.003738 |
| proteasome (prosome, macropain) subunit, beta type, 4 | D26600 | −1.39 | 0.004463 |
| ras-related C3 botulinum toxin substrate 1 (rho family, small GTP binding protein Rac1) | M29870 | −1.26 | 0.012621 |
| APEX nuclease (multifunctional DNA repair enzyme) | M80261 | −1.2 | 0.007584 |
| S-phase kinase-associated protein 1A (p19A) | U33760 | −1.42 | 0.002275 |
| non-metastatic cells 1, protein (NM23A) expressed in | X73066 | −1.23 | 0.010548 |
| RAN, member RAS oncogene family | M31469 | −1.4 | 0.007467 |
| COP9 (constitutive photomorphogenic, Arabidopsis, homolog) subunit 5 | U65928 | −1.38 | 0.002999 |
| platelet-derived growth factor receptor, alpha polypeptide | M21574 | 1.27 | 0.007996 |
| mitogen-activated protein kinase 10 | U07620 | −1.21 | 0.00607 |
| neural precursor cell expressed, developmentally down-regulated 8 | D23662 | −1.23 | 0.011055 |
| Ras homolog enriched in brain 2 | D78132 | −1.2 | 0.004309 |
| ubiquitin-conjugating enzyme E2N (UBC13 homolog, yeast) | D83004 | −1.33 | 0.003258 |
| RAP1, GTP-GDP dissociation stimulator 1 | X63465 | −1.54 | 0.009557 |
| Melanoma-associated antigen recognised by cytotoxic T lymphocytes | U19796 | −1.22 | 0.010698 |
| U50535 /FEATURE = /DEFINITION = HSU50535 Human BRCA2 region, mRNA sequence CG006 | U50535 | 1.23 | 0.009684 |
| protein tyrosine phosphatase, receptor type, A | M34668 | −1.25 | 0.015648 |
| heat shock protein 75 | U12595 | −1.31 | 0.005772 |
| proteasome (prosome, macropain) subunit, alpha type, 2 | D00760 | −1.3 | 0.008858 |
| proteasome (prosome, macropain) subunit, alpha type, 3 | D00762 | −1.39 | 0.012143 |
| somatostatin | J00306 | −1.31 | 0.012147 |
| transcription elongation factor B (SIII), polypeptide 1 (15 kD, elongin C) | L34587 | −1.32 | 0.00108 |
| replication protein A1 (70 kD) | M63488 | −1.25 | 0.01319 |
| X14675 /FEATURE = cds /DEFINITION = HSBCR3C Human bcr-abl mRNA 5 fragment (clone 3c) | X14675 | 1.27 | 0.011268 |
| retinoblastoma binding protein 4 | X74262 | −1.21 | 0.013161 |
| proteasome (prosome, macropain) subunit, beta type, 3 | D26598 | −1.24 | 0.000943 |
| proteasome (prosome, macropain) subunit, beta type, 2 | D26599 | −1.31 | 0.005831 |
| proteasome (prosome, macropain) subunit, beta type, 4 | D26600 | −1.33 | 0.001273 |
| proteasome (prosome, macropain) 26S subunit, non-ATPase, 8 | D38047 | −1.3 | 0.004844 |
| proteasome (prosome, macropain) subunit, beta type, 7 | D38048 | −1.35 | 0.002867 |
| proteasome (prosome, macropain) 26S subunit, non-ATPase, 1 | D44466 | −1.36 | 0.001895 |
| tyrosine 3-monooxygenase/tryptophan 5-monooxygenase activation protein, zeta polypeptide | M86400 | −1.47 | 0.010563 |
| cyclin-dependent kinase 5 | X66364 | −1.27 | 0.017644 |
| proteasome (prosome, macropain) 26S subunit, non-ATPase, 11 | AB003102 | −1.36 | 0.005788 |
| neuregulin 1 | L12260 | 1.21 | 0.009292 |
| histidine triad nucleotide binding protein | U51004 | −1.29 | 0.009004 |
| proteasome (prosome, macropain) 26S subunit, ATPase, 6 | D78275 | −1.49 | 0.002007 |
| Fk506-Binding Protein, Alt. Splice 2 | X52220 | −1.32 | 0.013334 |
| glycosylphosphatidylinositol specific phospholipase D1 | L11702 | 1.2 | 0.000988 |
| macrophage migration inhibitory factor (glycosylation-inhibiting factor) | L19686 | −1.36 | 0.000667 |
| FK506 binding protein 1A (12 kD) | M34539 | −1.25 | 0.008632 |
| ubiquitin carrier protein | M91670 | −1.28 | 0.014471 |
| glutathione-S-transferase like; glutathione transferase omega | U90313 | −1.3 | 0.015862 |
| v-crk sarcoma virus CT10 oncogene homolog (avian) | D10656 | −1.24 | 0.018048 |
| GDP dissociation inhibitor 2 | D13988 | −1.24 | 0.008673 |
| protease, serine, 11 (IGF binding) | D87258 | −1.21 | 0.019954 |
| proteasome (prosome, macropain) 26S subunit, ATPase, 1 | L02426 | −1.21 | 0.010531 |
| RAB5A, member RAS oncogene family | M28215 | −1.24 | 0.013948 |
| proteasome (prosome, macropain) 26S subunit, ATPase, 3 | M34079 | −1.26 | 0.001283 |
| polymerase (RNA) II (DNA directed) polypeptide L (7.6 kD) | U37690 | −1.27 | 0.000267 |
| tubulin, beta, 4 | U47634 | −1.38 | 0.008012 |
| tubulin, beta, 5 | X00734 | −1.37 | 0.008912 |
| casein kinase 2, beta polypeptide | X57152 | −1.24 | 0.013439 |
| dynamin 1-like | AF000430 | −1.3 | 0.009226 |
| basic transcription factor 3 | X53280 | −1.2 | 0.017502 |
| tubulin, alpha 1 (testis specific) | X06956 | −1.67 | 0.011897 |
| microtubule-associated protein tau | J03778 | −1.31 | 0.002685 |
| ubiquinol-cytochrome c reductase core protein I | L16842 | −1.4 | 0.004071 |
| H2A histone family, member O | L19779 | −1.22 | 0.012995 |
| calcium/calmodulin-dependent protein kinase I | L41816 | −1.29 | 0.007763 |
| S-adenosylmethionine decarboxylase 1 | M21154 | −1.28 | 0.019389 |
| protein kinase, cAMP-dependent, regulatory, type I, alpha (tissue specific extinguisher 1) | M33336 | −1.3 | 0.012561 |
| protein kinase, cAMP-dependent, regulatory, type I, alpha (tissue specific extinguisher 1) | M33336 | −1.33 | 0.013602 |
| IK cytokine, down-regulator of HLA II | S74221 | −1.23 | 0.012642 |
| ubiquitin-conjugating enzyme E2L 3 | S81003 | −1.29 | 0.011308 |
| aconitase 2, mitochondrial | U87939 | −1.26 | 0.011241 |

Figure 1A:
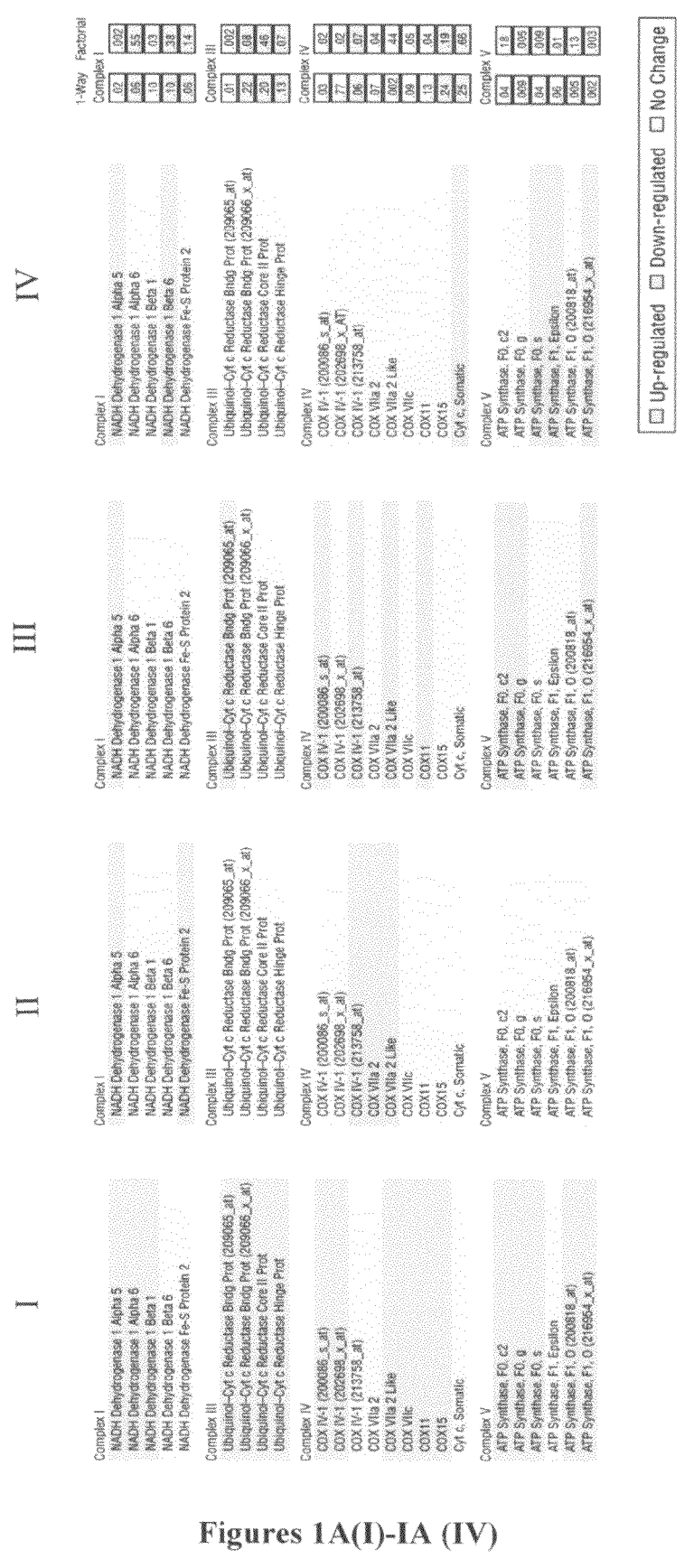

Expression of any polynucleotide, the corresponding polypeptide, or any combination thereof identified in Tables 1, 2, or 3, in FIGS. 1A(I)-1A(IV), or in FIGS. 6A-6D may be used as the basis for diagnostic or prognostic assays of the invention. Further, as many of the genes identified herein are involved in mitochondrial energy metabolism, expression of any gene whose polypeptide product is localized to the mitochondria and involved in energy metabolism may be used in the diagnostic and prognostic methods of the invention.

Stressing Cells

The diagnostic methods of the invention feature a step of stressing cells in a sample taken from a subject. Any technique for stressing cells known in the art may be used; such techniques include nutrient stress, oxygen stress, temperature stress, osmotic stress, or a combination thereof.

Nutrient stress can be achieved by subjecting cells to a lower availability of a vital nutrient such as glucose or sucrose as compared to standard cell culture conditions. For example, in the lymphocyte culture using RPMI-1640 media described herein, glucose is normally present at 2 g/l. Here, glucose depravation can accordingly be provided by culturing cells at reduced glucose concentrations (e.g., less than 2, 1.5, 1, 0.75, 0.5, 0.25, 0.1, or 0.05 g/l glucose). Nutrient stress, in any cell culture media system, can be achieved by a similar reduction of a vital nutrient.

Oxygen stress can be induced by either increasing or decreasing the oxygen available to cultured cells (e.g., $pO_2$ is generally 10-80 mm in normal tissues). Oxygen stress can be induced by decreasing the $pO_2$ to an amount lower than is normally observed, e.g., less than 40, 30, 20, 10, 5, 2, or 1 mm $pO_2$ or increasing the $pO_2$ above the normal levels, e.g., greater than 80, 90, 100, 110, 120, 130, 150, 170 mm $pO_2$. In another example, standard culture conditions typically include a 5% $CO_2$:20% $O_2$:75% $N_2$ atmosphere. By altering oxygen concentration, e.g., cultured in a reduced oxygen environment, where oxygen levels are less than 19%, 15%, 10%, 5%, 2%, or 1%, or in an increased oxygen environment, e.g., at least 21%, 23%, 25%, 28%, 30%, or 35% oxygen, the cells can be stressed.

Stress can also be induced by culturing cells at increased or decreased temperature. Typically, cells are cultured at 37° C. Low temperature stress can be induced by culturing at a temperature less than 35, 34, 32, 30, 28, 25, 22, or 20° C. Increased temperatures can involve culturing cells at, e.g., at least 39, 40, 42, 44, 46, 48, or 50° C.

Stress can also be induced by culturing cells at altered osmolarity, either by increasing or decreasing salt levels as compared to control samples. The salt which is increased or decreased will depend on the particular type of cell being cultured and the culture medium being used. Any biologically compatible salt known in the art can be added or any salt normally found in culture media can be removed to generate osmotic stress. In one example, using a lymphocyte culture as described below which employs RPMI-1640 media, the concentration of sodium chloride, which is normally 6 g/l, can be increased (e.g., at least 7, 8, 9, 10, 12, 15, or 20 g/l) or decreased (e.g., less than 5.5, 5, 4, 3, 2, 1, 0.5, 0.25 g/l) to produce osmotic stress.

An appropriate duration of a stress depends on the severity of the particular stress employed, and can be determined by one of skill in the art. Typically, the stress can be employed for at least 6, 12, 18, or 24 hours or at least 2, 3, 5, 6, 7, 10, 14, or 21 days. If multiple stresses are simultaneously employed (e.g., nutrient and temperature stress), either the length or severity of each individual stress required for diagnosis of a psychotic disorder can be reduced.

Measuring Gene or Protein Expression

Expression levels of particular nucleic acids or polypeptides can be correlated with a particular disease state, and thus are useful in diagnosis. Expression levels can be measured using any technique known in the art. The skilled artisan will understand that the particular method employed for measuring expression is not critical to the invention.

In one embodiment, a patient having a psychotic disorder (e.g., BPD or schizophrenia) will show an alteration in the expression of at least one of the nucleic acids listed in Table 1, Table 3, in FIGS. 1A(I)-1A(IV), or in FIGS. 6A-6D. In another embodiment, a patient having a psychotic disorder will have a particular expression profile that includes significantly decreased expression of two or more nuclear encoded mitochondrial metabolism nucleic acid molecules or proteasome associated nucleic acid molecules (e.g., those listed in Table 1, Table 3, in FIGS. 1A(I)-1A(IV), or in FIGS. 6A-6D) as compared to a normal control. Alterations in gene expression are detected using methods known to the skilled artisan and described herein.

In one embodiment, oligonucleotides or longer fragments derived from any of the nucleic acid sequences described herein (e.g., those listed in Table 1, Table 3, in FIGS. 1A(I)-1A(IV), or in FIGS. 6A-6D) may be used as targets in a microarray. The microarray is used to assay the expression level of large numbers of genes simultaneously and to identify genetic variants, mutations, and polymorphisms. Such information can be used to diagnose a psychotic disorder (e.g., BPD or schizophrenia).

In another embodiment, an alteration in the expression of a nucleic acid sequence described herein (e.g., those listed in Table 1, Table 3, in FIGS. 1A(I)-1A(IV), or in FIGS. 6A-6D) is detected using real-time quantitative PCR (Q-rt-PCR) to detect changes in gene expression. Q-rt-PCR methods are known in the art and are described herein.

In another embodiment, an antibody that specifically binds a polypeptides encoded by a nucleic acid described herein (e.g., listed in Table 1, Table 3, in FIGS. 1A(I)-1A(IV), or in FIGS. 6A-6D) may be used for the diagnosis of a psychotic disorder (e.g., BPD or schizophrenia). A variety of protocols for measuring an alteration in the expression of such polypeptides are known, including immunological methods (such as ELISAs and RIAs), and provide a basis for diagnosing a psychotic disorder (e.g., BPD or schizophrenia). Again, a decrease in the level of the polypeptide is diagnostic of a patient having a psychotic disorder (e.g., BPD or schizophrenia).

In yet another embodiment, hybridization with PCR probes that are capable of detecting at least one of the polynucleotide sequences listed in Table 1, Table 3, in FIGS. 1A(I)-1A(IV), or in FIGS. 6A-6D, including genomic sequences, or closely related molecules, can be used to hybridize to a nucleic acid sequence derived from a patient having a psychotic disorder (e.g., BPD or schizophrenia). The specificity of the probe, whether it is made from a highly specific region, e.g., the 5' regulatory region, or from a less specific region, e.g., a conserved motif, and the stringency of the hybridization or amplification (maximal, high, intermediate, or low), determine whether the probe hybridizes to a naturally occurring sequence, allelic variants, or other related sequences. Hybridization techniques can be used to identify mutations indicative of a psychotic disorder in genes listed in Table 1, Table 3, in FIGS. 1A(I)-1A(IV), or in FIGS. 6A-6D, or may be used to monitor expression levels of these genes (for example, by Northern analysis (Ausubel et al., *Current Protocols in Molecular Biology*, Wiley Interscience, New York, 1997)).

In yet another approach, humans can be diagnosed for a propensity to develop a psychotic disorder (e.g., BPD or schizophrenia) by direct analysis of the sequence of at least one of the nucleic acids listed in Table 1 or Table 3.

Quantitative Real Time PCR

Q-rt-PCR can be performed using any method known in the art. In one embodiment, cDNA was synthesized from 1 μg of total RNA with the Invitrogen SuperScript First-Strand Synthesis System for Q-rt-PCR (Invitrogen, Calif.), using oligo dT as the primer. A primer set for each gene was designed with the help of Primer 3 (available from the Massachusetts Institute of Technology, Cambridge, Mass.). Amplicons were designed to be between 100 and 200 base pairs in length. Melt curve analysis and polyacrylamide gel electrophoresis were used to confirm the specificity of each primer pair. The real-time Q-rt-PCR reaction was performed in the MJ RESEARCH DNA ENGINE OPTICON (MJ Research, Waltham, Mass.; Opticon Monitor Data Analysis Software v 1.4), with the DyNAmo SYBR Green Q-rt-PCR Kit (Finnzymes, Finland), according to the company protocol, in 25 μl volume, with 2.5 μl of 1:5 diluted cDNA samples and 0.3 μM primers. PCR cycling conditions were as follows: initially, samples were heated at 95° C. for 10 minutes, followed by 49 cycles of 94° C. for 30 seconds, 55° C. for 30 seconds, 72° C. for 30 seconds. Data were collected between 72° C. and 79° C., depending on amplicon melting temperature. A melt curve analysis was performed at the end of each Q-rt-PCR experiment. Dilution curves were generated for each primer in every experiment by diluting cDNA from a control sample 1:3 twice, yielding a dilution series of 1.00, 0.333, and 0.111. The log of the dilution value was plotted against the cycle threshold (CT) value. Blanks were run with each dilution curve to control for cross contamination. Dilution curves, blanks, and samples were run in duplicate. Reported values were normalized to the average of three internal standards, which are not regulated in the gene array analysis or in the Q-rt-PCR analysis (see Table 5).

Microarray Analysis

The methods of the invention can employ microarrays for determining expression of nucleic acids or polypeptides. Such techniques are known in the art and are described in US 2004/0248286. Any appropriate array technology known in the art can be used in the diagnostic and prognostic methods of the invention.

Monitoring a Subject with a Psychotic Disorder

In addition to diagnostic methods, the invention also features methods for monitoring the progression of a psychotic disorder in a subject. Such methods include obtaining a cell sample from the subject, subjecting a cell from the sample to stress, and measuring the expression of a polypeptide or polynucleotide in the cell. A second measurement of expression is subsequently performed using the same steps following a time interval (e.g., at least 1, 2, 5, 7, 14, or 28 days, or at least 1, 2, 3, 4, 5, 6, 8, 10, 12, or 24 months). The two measurements are then compared, where a change in expression is indicative of disease progression or improvement. In one example, an increase in a gene associated with mitochondrial function or electron transport is taken as an indication of the severity of the disorder decreasing.

Such monitoring methods can be performed in conjunction with administration of a therapy (e.g., pharmaceutical therapy such as those described herein) to the subject and, thus, can be used to determine if a particular therapy is having the desired effect on gene expression, which can be indicative of the severity of the psychotic disorder. In one example, the first measurement is taken prior to commencement of a therapy. Therapy is begun following the first measurement, and a second measurement is performed six months following the commencement of therapy. A change in the second measurement as compared to the first measurement can thus be taken as indication of the effectiveness of the therapy.

The following example is intended to illustrate, rather than limit, the invention.

TABLE 5

Entrez GeneID Numbers and Primer Sequences of Genes Chosen

| Genes of Interest | Respiratoy Chain Complex | Entrez GeneID No. | Forward Sequence | Reverse Sequence |
|---|---|---|---|---|
| Cytochrome c oxidase IV-1 (COX4I1) | IV | 1327 | CGAGCAATTTCCACCTCTGT (SEQ ID NO: 1) | CAGGAGGCCTTCTCCTTCTC (SEQ ID NO: 8) |
| ATP synthase, F0, c2 (ATP5G2) | V | 517 | TGGGATTGGAACTGTGTTTG (SEQ ID NO: 2) | TCACATGGCAAAGAGGATGA (SEQ ID NO: 9) |
| ATP synthase, F0, g (ATP5L) | V | 10632 | TGTTGTTGGACCATGTGTGA (SEQ ID NO: 3) | GCGGGCTAAACAGACGTGTA (SEQ ID NO: 10) |
| ATP synthase, F1, O (OSCP) | V | 539 | CTGAAGGAACCCAAAGTGG (SEQ ID NO: 4) | GAAAAGGCAGAAACGACTCC (SEQ ID NO: 11) |
| Control genes | | | | |
| Glyceraldehyde-3-phosphate dehydrogenase (GAPDH) | NA | 2597 | CTCCCATTCTTCCACCTTTG (SEQ ID NO: 5) | GTCCACCACCCTGTTGCT (SEQ ID NO: 12) |
| Keratin 10 | NA | 3858 | GGGCGAGTCTTCATCTAAGG (SEQ ID NO: 6) | AATGGTCTGTGTGAAGGGAGA (SEQ ID NO: 13) |
| Integral membrane protein 2A (ITM2A) | NA | 9452 | CATTCGTGAGGATGACAACA (SEQ ID NO: 7) | CAGCAACAAGTCCAGGTAAGC (SEQ ID NO: 14) |

Abbreviation: NA, not applicable.
*For array data, see FIGS. 1A(1)-1A(4).

Example 1

Differential Gene Expression in Lymphocytes from BPD Patients

We isolated lymphocytes from 20-30 ml of blood taken from normal controls and patients diagnosed with BPD according to the criteria of DSM IV (*DSM-IV, Diagnostic and Statistical Manual of Mental Disorder*, Fourth Ed., American Psychiatric Association, Washington, D.C., 1994). The *Structured Clinical Interview for DSM IV Axis I Disorders and the Brief Psychiatric Rating Scale* were used to verify diagnoses. For specifics on test subjects see FIG. 2. Lymphocytes were separated by centrifugation using Histopaque columns (Sigma-Aldrich, St. Louis, Mo.) and split into three batches. One batch was directly subjected to gene expression microarray analysis or alternatively, frozen at −80° C., whereas two batches were washed three times and cultured in either regular RPMI-1640 medium or low glucose RPMI-1640 medium (50% normal glucose content; 1 g/l) for a period of 5 days. The cultured cells were optionally frozen at −80° C. Cells were harvested; RNA was extracted (RNagents kit: Promega, Madison, Wis.), and cDNA was synthesized from 0.5 ng RNA and biotinylated RNA synthesized from cDNA (MessageAmp 11-96 kit; Ambion, Austin, Tex.). Biotinylated RNA was fragmented and hybridized to the HG-U133A 2.0 array (Affymetrix, Santa Clara, Calif.) overnight at 45° C. and stained on a washing station with two rounds of streptavidin-phycoerythrin (Molecular Probes, Eugene, Ore.) separated by a round of biotinylated antistreptavidin antibody (Vector Laboratories, Burlingame, Calif.). The fresh-frozen lymphocytes were worked up in one batch for gene array experiments. All of the cultured lymphocytes were worked up together in a separate batch with an improved protocol developed during the course of this project, for which the amount of input RNA could be lowered from 4 μg to 1 μg. Because of the small sample sizes and the variable amount of lymphocytes yielded from individual probands, a number of samples did not yield enough mRNA for gene array analysis (FIG. 2). The number of samples per group ranged from 10 to 17.

Gene expression levels were calculated with the RMA algorithm (Irizarry et al., *Biostatistics* 4:249-264, 2003) and compared using the comparison analysis of the dChip program, which computes P values based on the t distribution, with the degrees of freedom set according to the Welch-modified 2-sample t. test. Only samples that met quality control criteria provided by the GeneChip Operating Software (Affymetrix) and DNA-Chip Analyzer (dChip 2006) (Li and Wong, *Proc. Natl. Acad. Sci. USA* 98:31-36, 2001) were incorporated into the analysis (FIG. 2) (mean±SD noise, 0.9±0.1; mean±SD percentage present call, 56.2%±1.7%; mean±SD 3'-5' glyceraldehyde-3-phosphate dehydrogenase ratio, 1.4±0.4; mean±SD 3'-5' β-actin ratio, 1.6±0.8; mean±SD percentage of array outliers, 0.16%±0.22%; mean±SD percentage of single outliers, 0.046%±0.043%; no significant differences were observed between groups).

All genes differently expressed between two groups ($p<0.05$; >50% 'present' call; four groups: (I) low glucose: BPD over control; (II) normal glucose: BPD over control; (III) control: low over normal glucose; (IV) BPD: low over normal glucose) were subjected to a classification analysis using the Gene Ontology database gene product attributes (GO), calculated with the dChip software. Multiples of same transcripts were masked for classification analyses.

Similar results were obtained with log 2-transformed and natural scale data. Analysis of variance filtering was carried out in using dChip software. Permuted and adjusted P values for mitochondrial genes were obtained with the MAPPFinder program (Doniger et al., *Genome Biol.* 4:R7, 2003). We used 271 groupings (MAPPs) of individual genes for this analysis, grouped in a manner that avoided duplication of the same genes in independent groups. MAPPFinder calculates a non-parametric statistic based on 2000 permutations of the data, randomizing the gene associations for each sample to generate a distribution of z scores for each MAPP, which are then used to assign permuted P values. In addition, the Westfall-Young adjustment, which calculates the family wise error rate for each sample and accounts for multiple testing, is used for multiple testing. This adjustment gives the adjusted P value. Fisher exact test was used to examine the statistical difference between the percentage of regulation of mitochondrial transcripts vs. the percentage of regulation of all of the transcripts.

Families of genes, such as genes of the mitochondrial respiratory chain or genes specific for B or T cells, were compared between NC and BPD samples with 2-tailed, paired t tests using the natural expression values. For example, for the mitochondrial respiratory chain, the expression level of each of the 114 individual transcripts in an experimental group was divided by the average expression level of each transcript in all of the groups. False discovery rates were calculated in the dChip program by estimating the empirical false discovery rate for a group of genes (i.e., the 114 mitochondrial transcripts) using 2000 random permutations.

In the comparison of control and BPD lymphocytes in low glucose medium, the GO categories that had more hits for downregulated genes than would be expected by chance included 'mitochondrion' ($p=0$), 'cytochrome-c oxidase activity' ($p=0.0007$), 'mitochondrial electron transport chain' ($p=0.001$) and 'ubiquinol-cytochrome-c reductase activity' ($p=0.0001$). Further analyses revealed that 18 probe sets of electron transport transcripts, out of 114 on the array (see Table 7 for GenBank and Entrez Gene number of all 114 transcripts), were significantly lower expressed in BPD lymphocytes under glucose deprivation (FIG. 1A(I)), while none were expressed at higher levels. The 18 probe sets represented 15 individual mRNA transcripts, composing 19% of all electron transport probe sets on the array (35/114 probe sets were duplicate probe sets), while on average only 8.2% of probe sets were lower in BPD lymphocytes under glucose deprivation (FIG. 1B(I)). This difference was significant in Fisher exact test. Furthermore, the entire group of electron transport transcripts was shifted significantly in BPD toward lower expression levels (FIG. 1C(I) and Table 6).

TABLE 6

Statistics for the Entire Group of Mitochondrial Respiratory Chain Transcripts

| Comparison | P Value for 2-Tailed, Paired t Test of Expression % Values* | Up-regulation FDR, %† | Down-regulation FDR, %† |
|---|---|---|---|
| Low glucose, NC‡ vs BPD§ | <.001 | ≦6 | Not calculable |
| Normal glucose, NC‡ vs BPD§ | 0.21 | ≦33 | ≦50 |
| BPD, normal‡ vs low§ glucose | 0.62 | Not calculable | ≦17 |

TABLE 6-continued

Statistics for the Entire Group of Mitochondrial Respiratory Chain Transcripts

| Comparison | P Value for 2-Tailed, Paired t Test of Expression % Values* | Up-regulation FDR, %† | Down-regulation FDR, %† |
|---|---|---|---|
| NC, normal‡ vs low§ glucose | <.001 | ≦12 | Not calculable |
| Fresh lymphocytes, NC‡ vs BPD§ | 0.05 | ≦100 | ≦17 |

Abbreviations:
BPD, bipolar disorder;
FDR, false discovery rate;
NC, normal control.
*Values are for genes of the mitochondrial respiratory chain (for GeneID numbers, see eTable 1 [http://www.archgenpsychiatry.com]). For percentage expression values, the expression level of each of the 114 individual transcripts in an experimental group was divided by the average expression level of this transcript in all of the groups.
†The FDRs were calculated in the dChip program (http://biosun1.harvard.edu/complab/dchip) by estimating the empirical FDR using 2000 random permutations.
‡Baseline group.
§Experimental group.

Figure 3B:
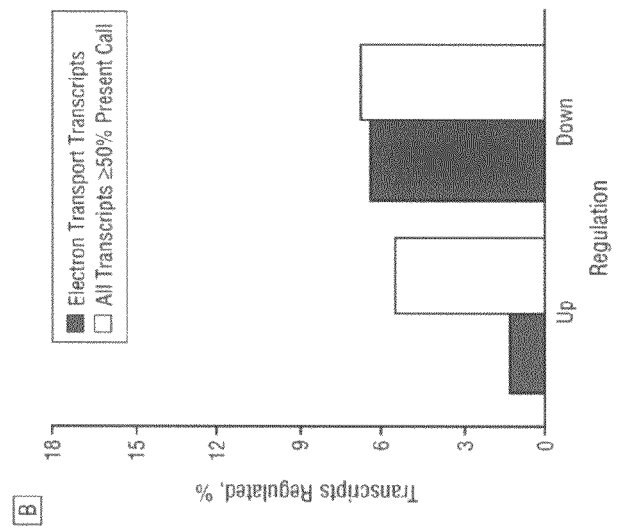
Figure 3C:
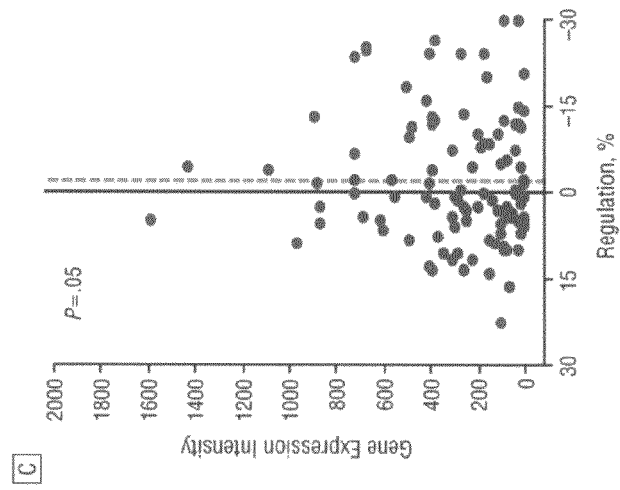
Figures 4A, 4B:
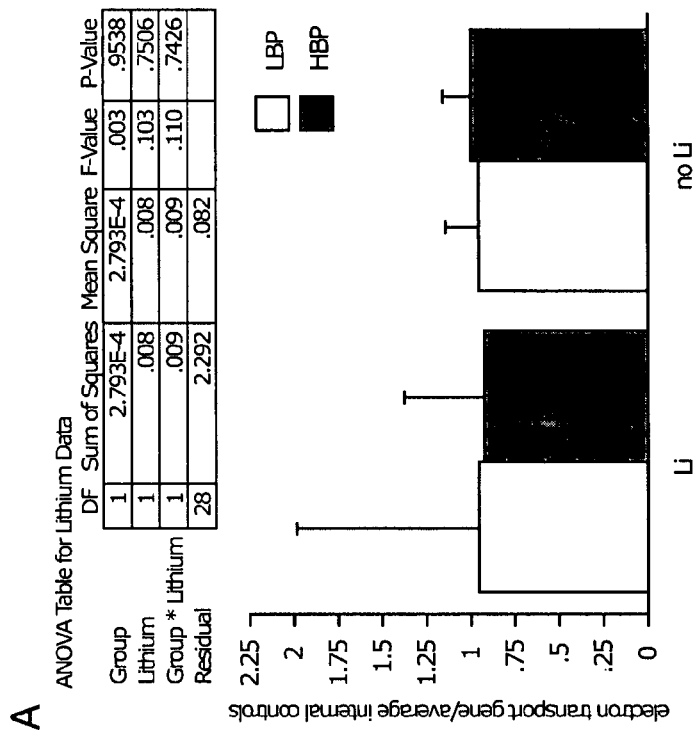
FIGS. 4A-4E are graphs showing ANOVA data for BPD subjects to test for effects of Li (FIG. 4A), VPA (FIG. 4B), antiepileptics (FIG. 4C), antipsychotics (FIG. 4D), and antidepressants (FIG. 4E). Tables show ANOVA5 for samples grouped by glucose concentration (low versus normal), and ANOVA5 for interactions with drugs. Error bars represent a 95% confidence interval.
Figures 4C, 4D:
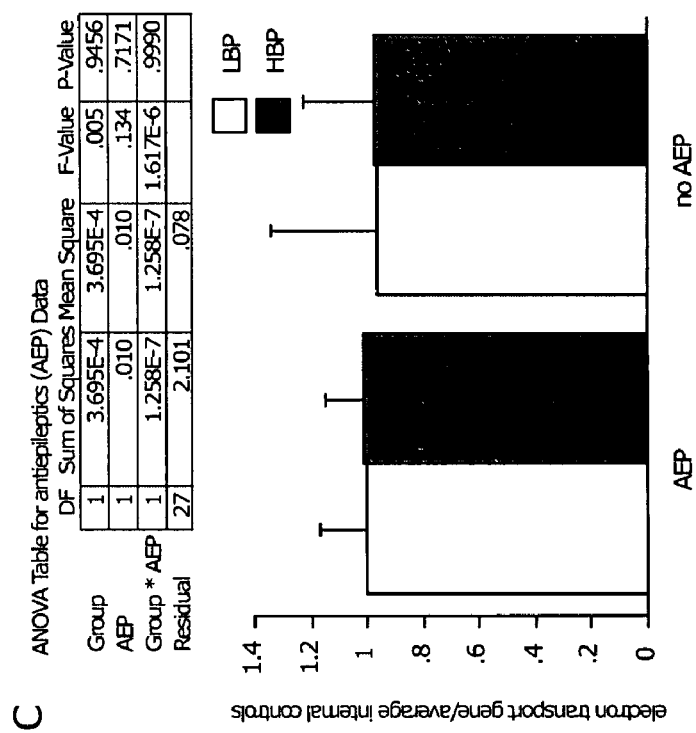
Figure 4E:
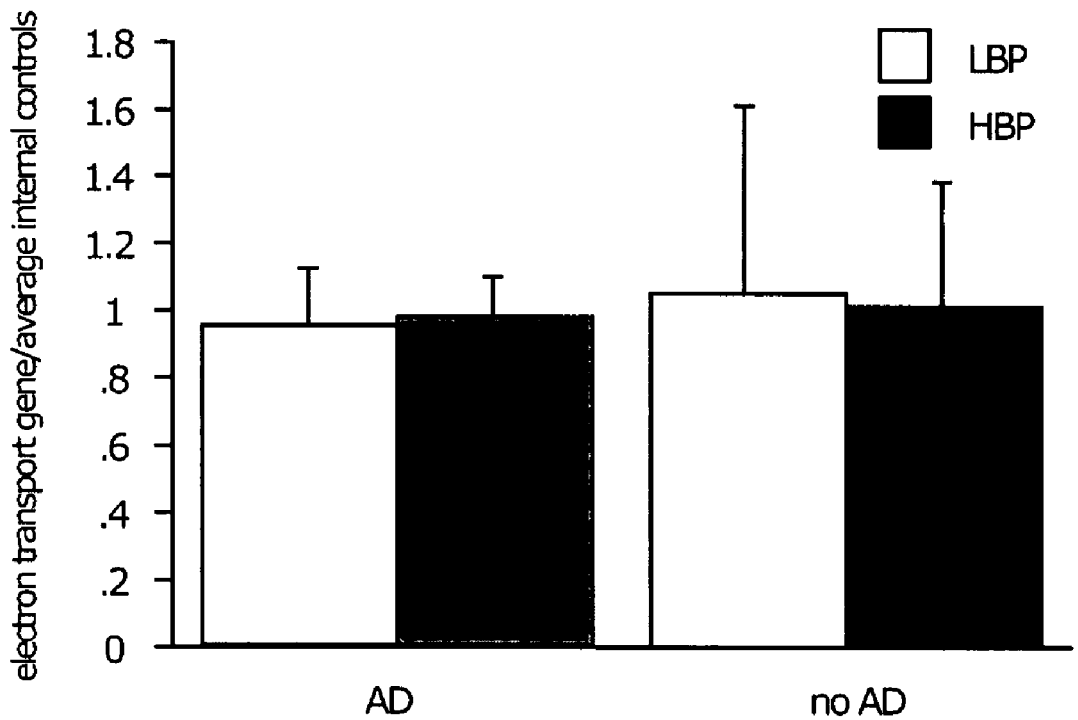
Figure 5:
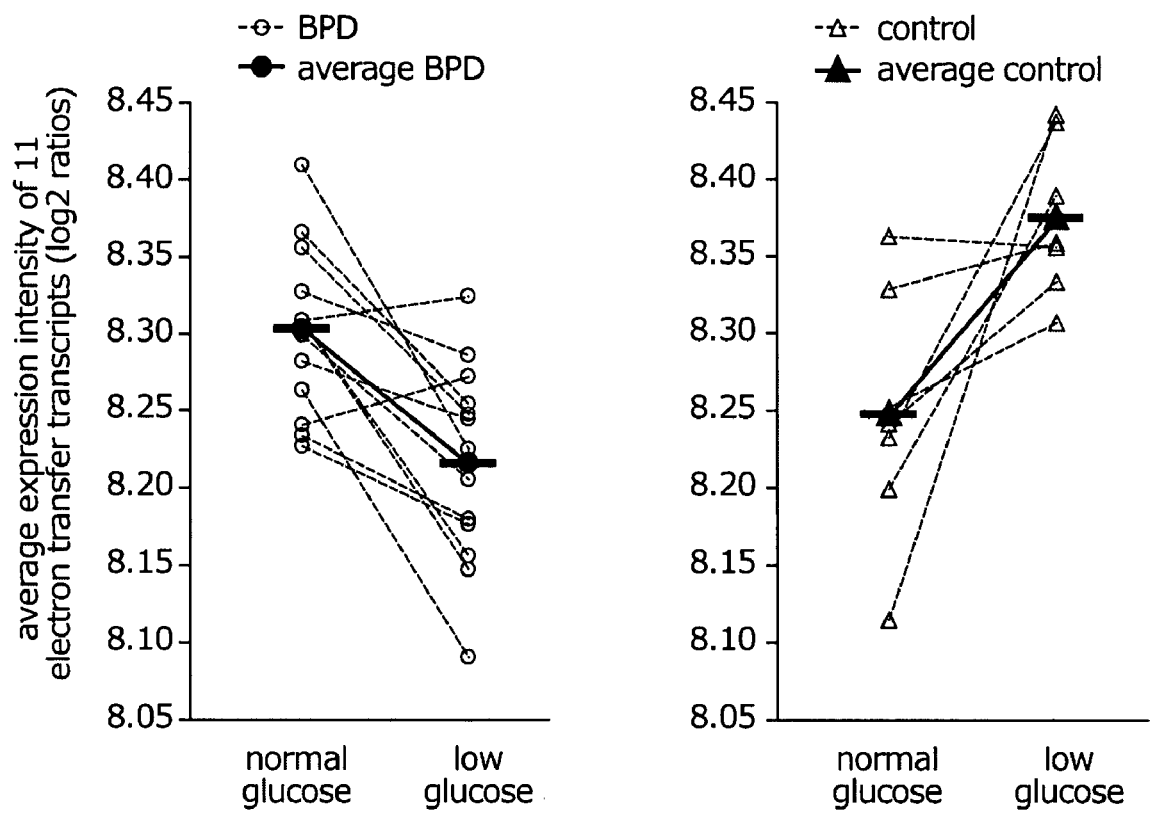
FIG. 5 is a set of graphs showing pairwise comparison of 13 bipolar disorder (BPD) lymphocyte samples in normal and low-glucose medium (left) as well as 7 normal control (NC) lymphocyte samples in normal and low-glucose medium (right). Analysis of variance filtering (factorial analysis of variance, glucose concentration×treatment) was used to select electron transport transcripts with high variations between the groups. Fifteen transcripts survived the filtering and their logarithm-transformed values were averaged for each paired sample (n=13 for BPD; n=7 for NCs). Bipolar disorder lymphocytes showed a down-regulation of these transcripts under low-glucose stress ($P \leq 0.003$, paired t test), whereas NC lymphocytes showed an up-regulation of these transcripts ($P \leq 0.02$, paired t test). Dashed line indicates pair; solid line, average of group.
Figures 6A, 6B, 6C, 6D, 6E:
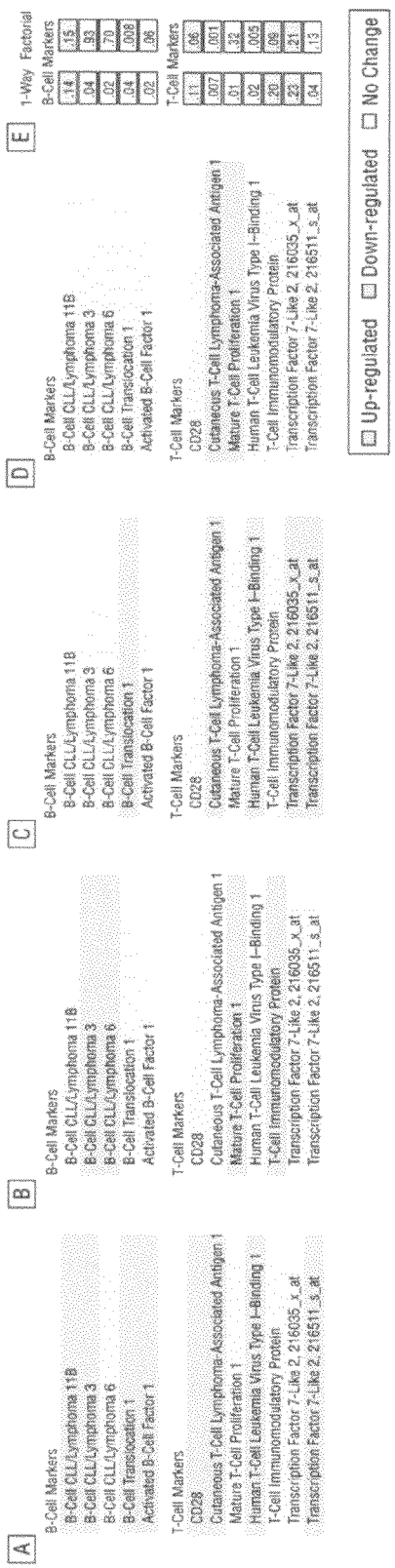
FIGS. 6A-6E show individual B-cell and T-cell markers that were regulated in the comparison between low glucose for bipolar disorder lymphocytes and low glucose for normal control lymphocytes (FIG. 6A), normal glucose for bipolar disorder lymphocytes and normal glucose for control lymphocytes (FIG. 6B), low and normal glucose for normal control lymphocytes (FIG. 6C), and low and normal glucose for bipolar disorder lymphocytes (FIG. 6D).
Figures 7A, 7B, 7C, 7D:
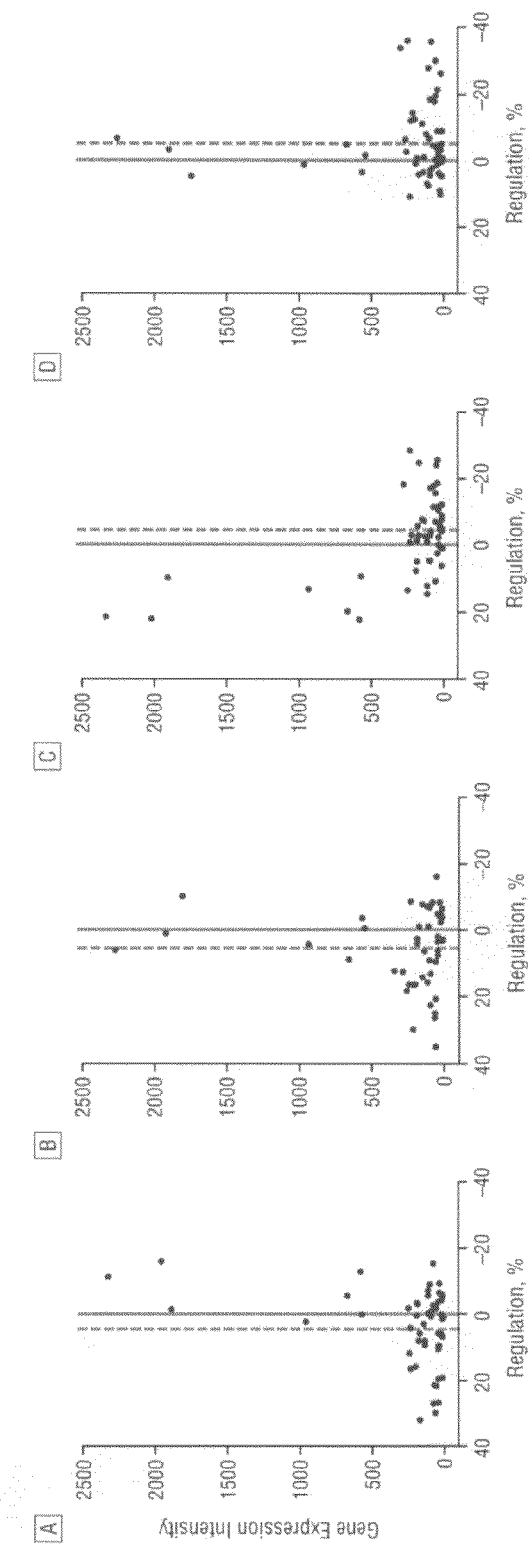
FIGS. 7A-7D are graphs showing regulation of the entire group of 54 B-cell markers. Expression levels of each individual probe set were compared between low glucose for bipolar disorder lymphocytes and low glucose for normal control lymphocytes (FIG. 7A), normal glucose for bipolar disorder lymphocytes and normal glucose for normal control lymphocytes (FIG. 7B), low and normal glucose for normal control lymphocytes (FIG. 7C), and low and normal glucose for bipolar disorder lymphocytes (FIG. 7D). Solid line indicates equal regulation; dashed line, actual average regulation of all transcripts. See Table 9 for all GeneID numbers.
Figures 8A, 8B, 8C, 8D:
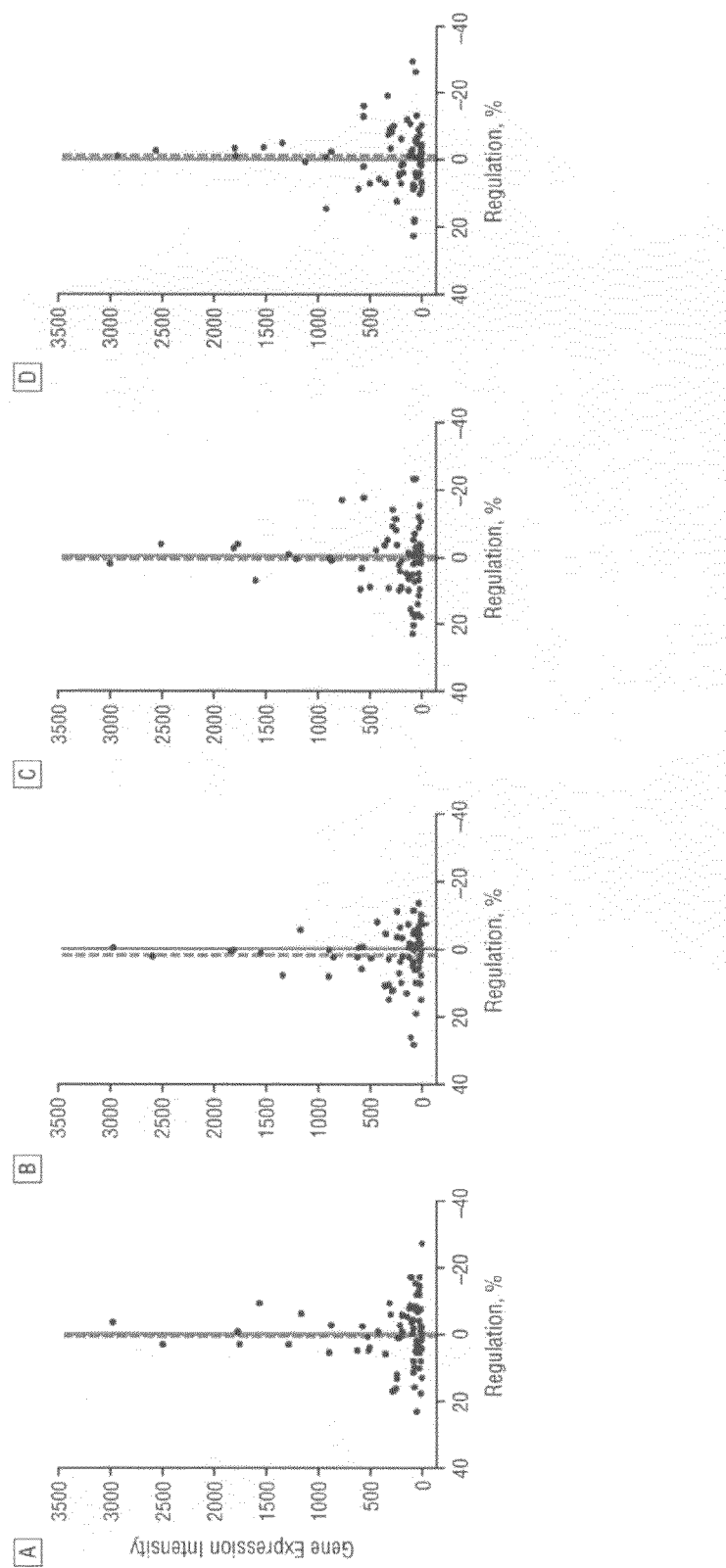
FIGS. 8A-8D are graphs showing regulation of the entire group of 77 T-cell markers. Expression levels of each individual probe set were compared between low glucose for bipolar disorder lymphocytes and low glucose for normal control lymphocytes (FIG. 8A), normal glucose for bipolar disorder lymphocytes and normal glucose for normal control lymphocytes (FIG. 8B), low and normal glucose for normal control lymphocytes (FIG. 8C), and low and normal glucose for bipolar disorder lymphocytes (FIG. D). Solid line indicates equal regulation; dashed line, actual average regulation of all transcripts. See Table 9 for all GeneID numbers.

No differences between BPD and control lymphocytes were observed either under normal glucose concentrations (FIGS. 1A(II), 1B(II), 1C(II)), or in fresh, uncultured lymphocytes (FIGS. 3A-3C). The difference in the expression level of electron transport transcripts between BPD and control subjects seems to be caused by a different molecular response to glucose deprivation. While control subjects showed an upregulation of these transcripts in response to energy stress (FIGS. 1A(III), 1B(III), 1C(III)), BPD subjects have a tendency to downregulate these transcripts (FIGS. 1A(IV), 1B(IV), 1C(IV)). Upregulated transcripts in control lymphocytes in low glucose medium, compared to control lymphocytes in normal glucose medium, had significant hits in the GO categories of 'mitochondrion' (p=0.002) and 'cytochrome-c oxidase activity' (p=0.002), while downregulated transcripts in BPD lymphocytes in low glucose medium, compared to BPD lymphocytes in normal glucose medium, had a significant hit in the GO category of 'mitochondrion' (p=0.01). While the entire group of electron transport transcripts was significantly shifted toward upregulation in the control lymphocytes under glucose deprivation stress (FIG. 1C(III)), no significant shift toward downregulation was observed in the BPD lymphocytes under energy stress (FIG. 1C(IV)). Regulation trends were verified with real-time quantitative PCR (Q-rt-PCR; FIGS. 1D(I) to 1D(IV)), carried out as previously described (C. Konradi et al., Arch. Sen. Psychiatry 61:300-308, 2004, MacDonald et al., Biol. Psychiatry 57:1041-1051, 2005). All values were normalized to an average of three internal control genes: integral membrane protein 2A (accession number: NM_004867), glyceraldehyde-3-phosphate dehydrogenase (GeneID-2597), and Keratin 10 (accession number NM_000421). Control genes were not regulated. Four electron-transport transcripts that were used to verify the gene array data replicated the major patterns observed in the gene array analysis (FIGS. 1D(I)-1D(IV)), although the levels of difference seen in the gene expression microarray study are at the threshold of detectability for Q-rt-PCR. When the analysis was limited to paired samples (n=13 for subjects with BPD, n=7 for NCs; see FIG. 2 for pairs), 15 transcripts showed high between-group variability as determined in a factorial analysis of variance (Table 8). These 15 transcripts were averaged and plotted (FIG. 5). In BPD lymphocytes, these transcripts were down-regulated under low-glucose stress (P≦0.003, paired t test), whereas in NC lymphocytes, these transcripts were up-regulated (P≦0.02, paired t test). In the paired samples, a comparison of NC and BPD lymphocyte mRNA expression levels in low glucose showed that 17 transcripts were expressed significantly lower in BPD lymphocytes, similar to the larger sample. Finally, no significant relationship between electron transfer transcript expression and medication was found when mitochondrial expression levels obtained in the gene arrays were plotted against drug treatment in a hierarchical cluster analysis or when analyses of variance were calculated (each group of drug compared with absence of that drug in low and normal glucose) using qPCR data (data not shown).

TABLE 7

All Nuclear Transcripts of the Mitochondrial Respiratory Chain Used for Analysis in FIGS. 1-4

| gene | GB Accession # | LocusLink ID | Affymetrix probe set ID | low glucose: BPD/control | | normal glucose: BPD/control | |
|---|---|---|---|---|---|---|---|
| | | | | fold change (natural) | p-value (log 2) | fold change (natural) | p-value (log 2) |
| Complex I | | | | | | | |
| NADH dehydrogenase 1 alpha, 1, 7.5 kDa | NM_004541 | 4694 | 202298_at | −1.00 | 0.943 | −1.01 | 0.750 |
| NADH dehydrogenase 1 alpha, 2, 8 kDa | BC003674 | 4695 | 209224_s_at | −1.06 | 0.320 | 1.17 | 0.040 |
| NADH dehydrogenase 1 alpha, 3, 9 kDa | NM_004542 | 4696 | 218563_at | −1.01 | 0.908 | −1.00 | 0.968 |
| NADH dehydrogenase 1 alpha, 4, 9 kDa | NM_002489 | 4697 | 217773_s_at | −1.03 | 0.389 | 1.02 | 0.600 |

TABLE 7-continued

All Nuclear Transcripts of the Mitochondrial Respiratory Chain Used for Analysis in FIGS. 1-4

| gene | GB Accession # | LocusLink ID | Affymetrix probe set ID | low glucose: BPD/control | | normal glucose: BPD/control | |
|---|---|---|---|---|---|---|---|
| | | | | fold change (natural) | p-value (log 2) | fold change (natural) | p-value (log 2) |
| NADH dehydrogenase 1 alpha, 5, 13 kDa | NM_005000 | 4698 | 201304_at | −1.15 | 0.035 | −1.08 | 0.043 |
| NADH dehydrogenase 1 alpha, 5, 13 kDa | AK022209 | 4698 | 215850_s_at | −1.06 | 0.527 | −1.06 | 0.149 |
| NADH dehydrogenase 1 alpha, 6, 14 kDa | BC002772 | 4700 | 202000_at | −1.10 | 0.025 | −1.06 | 0.340 |
| NADH dehydrogenase 1 alpha, 6, 14 kDa | BC002772 | 4700 | 202001_s_at | −1.01 | 0.828 | 1.05 | 0.222 |
| NADH dehydrogenase 1 alpha, 7, 14.5 kDa | NM_005001 | 4701 | 202785_at | −1.05 | 0.610 | −1.02 | 0.705 |
| NADH dehydrogenase 1 alpha, 8, 19 kDa | NM_014222 | 4702 | 218160_at | −1.04 | 0.484 | 1.01 | 0.832 |
| NADH dehydrogenase 1 alpha, 9, 39 kDa | AF050641 | 4704 | 208969_at | −1.01 | 0.970 | −1.01 | 0.628 |
| NADH dehydrogenase 1 alpha, 10, 42 kDa | NM_004544 | 4705 | 217860_at | −1.01 | 0.886 | 1.02 | 0.727 |
| NADH dehydrogenase 1 alpha, assembly factor 1 | NM_016013 | 51103 | 204125_at | −1.02 | 0.667 | 1.08 | 0.086 |
| NADH dehydrogenase 1 beta, 1, 7 kDa | NM_004545 | 4707 | 206790_s_at | −1.09 | 0.011 | −1.04 | 0.472 |
| NADH dehydrogenase 1 beta, 2, 8 kDa | NM_004546 | 4708 | 218200_s_at | 1.02 | 0.615 | 1.02 | 0.577 |
| NADH dehydrogenase 1 beta, 2, 8 kDa | NM_004546 | 4708 | 218201_at | −1.02 | 0.743 | 1.03 | 0.225 |
| NADH dehydrogenase 1 beta, 3, 12 kDa | NM_002491 | 4709 | 203371_s_at | −1.05 | 0.223 | −1.00 | 0.942 |
| NADH dehydrogenase 1 beta, 4, 15 kDa | NM_004547 | 4710 | 218226_s_at | −1.03 | 0.305 | −1.02 | 0.515 |
| NADH dehydrogenase 1 beta, 5, 16 kDa | NM_002492 | 4711 | 203621_at | −1.05 | 0.115 | 1.02 | 0.495 |
| NADH dehydrogenase 1 beta, 6, 17 kDa | NM_002493 | 4712 | 203613_s_at | −1.05 | 0.172 | −1.01 | 0.776 |
| NADH dehydrogenase 1 beta, 7, 18 kDa | NM_004146 | 4713 | 202839_s_at | 1.00 | 0.860 | −1.08 | 0.054 |
| NADH dehydrogenase 1 beta, 7, 18 kDa | M33374 | 4713 | 211407_at | 1.02 | 0.597 | 1.02 | 0.567 |
| NADH dehydrogenase 1 beta, 8, 19 kDa | NM_005004 | 4714 | 201226_at | −1.02 | 0.689 | 1.02 | 0.548 |
| NADH dehydrogenase 1 beta, 8, 19 kDa | NM_005004 | 4714 | 201227_s_at | −1.05 | 0.339 | 1.00 | 0.987 |
| NADH dehydrogenase 1 beta, 8, 19 kDa | AA723057 | 4714 | 214241_at | 1.14 | 0.360 | −1.01 | 0.863 |
| NADH dehydrogenase 1 beta, 11, 17.3 kDa | NM_019056 | 54539 | 218320_s_at | −1.07 | 0.195 | 1.05 | 0.225 |
| NADH dehydrogenase 1, alpha/beta, 1, 8 kDa | NM_005003 | 4706 | 202077_at | −1.04 | 0.310 | 1.00 | 0.890 |
| NADH dehydrogenase 1, unknown, 1, 6 kDa | NM_002494 | 4717 | 203478_at | −1.08 | 0.073 | −1.01 | 0.703 |
| NADH dehydrogenase 1, unknown, 2, 14.5 kDa | NM_004549 | 4718 | 218101_s_at | −1.06 | 0.215 | 1.02 | 0.789 |
| NADH dehydrogenase Fe—S protein 1, 75 kDa | NM_005006 | 4719 | 203039_s_at | −1.05 | 0.234 | −1.04 | 0.433 |
| NADH dehydrogenase Fe—S protein 2, 49 kDa | NM_004550 | 4720 | 201966_at | −1.01 | 0.543 | −1.12 | 0.183 |
| NADH dehydrogenase Fe—S protein 3, 30 kDa | NM_004551 | 4722 | 201740_at | −1.01 | 0.769 | 1.02 | 0.435 |
| NADH dehydrogenase Fe—S protein 4, 18 kDa | BC005270 | 4724 | 209303_at | −1.08 | 0.083 | −1.00 | 0.983 |
| NADH dehydrogenase Fe—S protein 5, 15 kDa | NM_004552 | 4725 | 201757_at | −1.06 | 0.197 | −1.03 | 0.285 |
| NADH dehydrogenase Fe—S protein 6, 13 kDa | NM_004553 | 4726 | 203606_at | −1.02 | 0.768 | 1.02 | 0.742 |
| NADH dehydrogenase Fe—S protein 7, 20 kDa | BC005954 | 374291 | 211752_s_at | −1.02 | 0.713 | −1.05 | 0.189 |
| NADH dehydrogenase Fe—S protein 8, 23 kDa | NM_002496 | 4728 | 203189_s_at | −1.03 | 0.384 | −1.00 | 0.980 |
| NADH dehydrogenase Fe—S protein 8, 23 kDa | NM_002496 | 4728 | 203190_at | −1.03 | 0.300 | −1.01 | 0.660 |
| NADH dehydrogenase flavoprotein 1, 51 kDa | AF092131 | 4723 | 208714_at | 1.02 | 0.565 | 1.04 | 0.389 |

TABLE 7-continued

All Nuclear Transcripts of the Mitochondrial Respiratory Chain Used for Analysis in FIGS. 1-4

| gene | GB Accession # | LocusLink ID | Affymetrix probe set ID | low glucose: BPD/control | | normal glucose: BPD/control | |
|---|---|---|---|---|---|---|---|
| | | | | fold change (natural) | p-value (log 2) | fold change (natural) | p-value (log 2) |
| NADH dehydrogenase flavoprotein 2, 24 kDa | NM_021074 | 4729 | 202941_at | 1.03 | 0.458 | −1.03 | 0.609 |
| Complex II | | | | | | | |
| succinate dehydrogenase complex, A, flavoprotein (Fp) | NM_004168 | 6389 | 201093_x_at | 1.04 | 0.341 | 1.01 | 0.819 |
| succinate dehydrogenase complex, A, flavoprotein (Fp) | AI348006 | 255812,6389 | 222021_x_at | −1.02 | 0.579 | −1.03 | 0.498 |
| succinate dehydrogenase complex, B, iron sulfur (Ip) | NM_003000 | 6390 | 202675_at | 1.03 | 0.491 | 1.00 | 0.900 |
| succinate dehydrogenase complex, B, iron sulfur (Ip) | AW294107 | 6390 | 214166_at | 1.02 | 0.872 | 1.07 | 0.178 |
| succinate dehydrogenase complex, C, 15 kDa | NM_003001 | 6391 | 202004_x_at | 1.02 | 0.742 | −1.12 | 0.099 |
| succinate dehydrogenase complex, C, 15 kDa | BG110532 | 6391 | 215088_s_at | −1.05 | 0.276 | 1.04 | 0.326 |
| succinate dehydrogenase complex, C, 15 kDa | AF080579 | 6391 | 216591_s_at | −1.15 | 0.437 | −1.16 | 0.431 |
| succinate dehydrogenase complex, D | NM_003002 | 6392 | 202026_at | −1.04 | 0.340 | 1.10 | 0.070 |
| Complex III | | | | | | | |
| ubiquinol-cytochrome c reductase binding protein | NM_006294 | 7381 | 205849_s_at | −1.06 | 0.058 | 1.02 | 0.386 |
| ubiquinol-cytochrome c reductase binding protein | BC005230 | 7381 | 209065_at | −1.20 | 0.000 | 1.07 | 0.290 |
| ubiquinol-cytochrome c reductase binding protein | M26700 | 7381 | 209066_x_at | −1.06 | 0.026 | 1.01 | 0.692 |
| ubiquinol-cytochrome c reductase complex (7.2 kD) | NM_013387 | 29796 | 218190_s_at | −1.02 | 0.670 | −1.01 | 0.828 |
| ubiquinol-cytochrome c reductase core protein I | NM_003365 | 7384 | 201903_at | 1.07 | 0.214 | −1.07 | 0.118 |
| ubiquinol-cytochrome c reductase core protein II | NM_003366 | 7385 | 200883_at | −1.09 | 0.036 | −1.04 | 0.562 |
| ubiquinol-cytochrome c reductase core protein II | AV727381 | 7385 | 212600_s_at | −1.07 | 0.073 | −1.05 | 0.327 |
| ubiquinol-cytochrome c reductase hinge protein | NM_006004 | 7388 | 202233_s_at | −1.09 | 0.026 | 1.01 | 0.853 |
| ubiquinol-cytochrome c reductase, 6.4 kDa | NM_006830 | 10975 | 202090_s_at | −1.06 | 0.166 | 1.03 | 0.432 |
| ubiquinol-cytochrome c reductase, Rieske iron-sulfur 1 | BC000649 | 7386 | 208909_at | −1.01 | 0.560 | −1.04 | 0.159 |
| Complex IV | | | | | | | |
| cytochrome c oxidase IV | AA854966 | 1327 | 200086_s_at | −1.08 | 0.000 | 1.01 | 0.722 |
| cytochrome c oxidase IV | NM_001861 | 1327 | 202698_x_at | −1.05 | 0.010 | −1.04 | 0.104 |
| cytochrome c oxidase IV | AW337510 | 1327 | 213758_at | −1.03 | 0.733 | 1.13 | 0.014 |
| cytochrome c oxidase Va | NM_004255 | 9377 | 203663_s_at | −1.00 | 0.982 | −1.02 | 0.705 |
| cytochrome c oxidase Vb | NM_001862 | 1329 | 202343_x_at | 1.01 | 0.752 | −1.02 | 0.517 |
| cytochrome c oxidase Vb | BC006229 | 1329 | 211025_x_at | −1.02 | 0.855 | −1.03 | 0.529 |
| cytochrome c oxidase Vb | AI557312 | 1329 | 213735_s_at | −1.04 | 0.568 | 1.01 | 0.839 |
| cytochrome c oxidase Vb | AI557312 | 1329 | 213736_at | −1.25 | 0.192 | 1.07 | 0.694 |
| cytochrome c oxidase VIa 1 | NM_004373 | 1337 | 200925_at | 1.00 | 0.864 | 1.02 | 0.558 |
| cytochrome c oxidase VIa 2 | NM_005205 | 1339 | 206353_at | 1.01 | 0.749 | −1.03 | 0.625 |
| cytochrome c oxidase VIb 1 (ubiquitous) | NM_001863 | 1340 | 201441_at | −1.03 | 0.558 | −1.01 | 0.754 |
| cytochrome c oxidase VIc | NM_004374 | 1345 | 201754_at | −1.06 | 0.098 | −1.03 | 0.383 |
| cytochrome c oxidase VIIa 2 (liver) | NM_001865 | 1347 | 201597_at | −1.02 | 0.684 | 1.11 | 0.018 |
| cytochrome c oxidase VIIa 2 like | NM_004718 | 9167 | 201256_at | −1.08 | 0.014 | −1.05 | 0.041 |
| cytochrome c oxidase VIIb | NM_001866 | 1349 | 202110_at | −1.00 | 0.963 | 1.05 | 0.271 |
| cytochrome c oxidase VIIc | NM_001867 | 1350 | 201134_x_at | −1.05 | 0.136 | −1.01 | 0.774 |
| cytochrome c oxidase VIIc | AA382702 | 1350 | 213846_at | −1.09 | 0.159 | −1.01 | 0.822 |
| cytochrome c oxidase VIIc | AF042165 | 1350 | 217491_x_at | −1.07 | 0.019 | 1.01 | 0.753 |
| cytochrome c oxidase 8A (ubiquitous) | NM_004074 | 1351 | 201119_s_at | 1.01 | 0.803 | 1.03 | 0.335 |
| cytochrome c, somatic | BC005299 | 54205 | 208905_at | −1.03 | 0.567 | −1.00 | 0.980 |
| cytochrome c-1 | NM_001916 | 1537 | 201066_at | 1.07 | 0.155 | 1.02 | 0.491 |
| COX10 homolog | NM_001303 | 1352 | 203858_s_at | 1.00 | 0.990 | 1.03 | 0.564 |

TABLE 7-continued

All Nuclear Transcripts of the Mitochondrial Respiratory Chain Used for Analysis in FIGS. 1-4

| gene | GB Accession # | LocusLink ID | Affymetrix probe set ID | low glucose: BPD/control | | normal glucose: BPD/control | |
|---|---|---|---|---|---|---|---|
| | | | | fold change (natural) | p-value (log 2) | fold change (natural) | p-value (log 2) |
| COX11 homolog | NM_004375 | 1353 | 203551_s_at | −1.15 | 0.132 | −1.00 | 0.938 |
| COX11 homolog | BC005895 | 1353 | 211727_s_at | −1.12 | 0.011 | 1.03 | 0.588 |
| COX15 homolog | NM_004376 | 1355 | 219547_at | −1.04 | 0.391 | 1.06 | 0.130 |
| COX15 homolog | BC002382 | 1355 | 221550_at | −1.15 | 0.036 | −1.02 | 0.946 |
| Complex V | | | | | | | |
| ATP synthase mitochondrial F1 complex assembly factor 2 | AW118608 | 91647 | 213057_at | 1.09 | 0.159 | 1.09 | 0.091 |
| ATP synthase mitochondrial F1 complex assembly factor 2 | AF070584 | 91647 | 214330_at | 1.03 | 0.554 | 1.02 | 0.617 |
| ATP synthase, alpha, , cardiac muscle | AI587323 | 498 | 213738_s_at | −1.03 | 0.150 | −1.01 | 0.689 |
| ATP synthase, b | BC005960 | 515 | 211755_s_at | −1.01 | 0.693 | −1.02 | 0.479 |
| ATP synthase, beta | NM_001686 | 506 | 201322_at | 1.03 | 0.266 | −1.02 | 0.572 |
| ATP synthase, c (subunit 9) | AL080089 | 516 | 208972_s_at | −1.01 | 0.901 | 1.02 | 0.792 |
| ATP synthase, c (subunit 9) isoform 2 | D13119 | 517 | 208764_s_at | −1.07 | 0.045 | 1.00 | 0.970 |
| ATP synthase, c (subunit 9) isoform 3 | NM_001689 | 518 | 207507_s_at | −1.02 | 0.731 | −1.01 | 0.921 |
| ATP synthase, c (subunit 9) isoform 3 | NM_001689 | 518 | 207508_at | −1.00 | 0.929 | 1.01 | 0.795 |
| ATP synthase, d | AF061735 | 10476 | 210149_s_at | −1.05 | 0.286 | −1.01 | 0.727 |
| ATP synthase, delta | NM_001687 | 513 | 203926_x_at | 1.01 | 0.897 | 1.02 | 0.734 |
| ATP synthase, delta | BE798517 | 513 | 213041_s_at | 1.05 | 0.401 | 1.06 | 0.285 |
| ATP synthase, e | NM_007100 | 521 | 207335_x_at | −1.08 | 0.144 | −1.01 | 0.887 |
| ATP synthase, e | BC003679 | 521 | 209492_x_at | −1.05 | 0.311 | −1.02 | 0.507 |
| ATP synthase, epsilon | NM_006886 | 514 | 217801_at | −1.06 | 0.068 | 1.06 | 0.102 |
| ATP synthase, f, isoform 2 | NM_004889 | 9551 | 202961_s_at | −1.00 | 0.967 | −1.04 | 0.377 |
| ATP synthase, F6 | NM_001685 | 522 | 202325_s_at | −1.04 | 0.381 | 1.02 | 0.513 |
| ATP synthase, g | NM_006476 | 10632 | 207573_x_at | −1.03 | 0.373 | 1.02 | 0.655 |
| ATP synthase, g | AA917672 | 10632 | 208745_at | −1.14 | 0.001 | 1.03 | 0.537 |
| ATP synthase, g | AF070655 | 10632 | 208746_x_at | −1.04 | 0.229 | 1.00 | 0.931 |
| ATP synthase, g | AL050277 | 10632 | 210453_x_at | −1.04 | 0.252 | 1.00 | 0.984 |
| ATP synthase, gamma 1 | NM_005174 | 509 | 205711_x_at | −1.00 | 0.892 | −1.05 | 0.061 |
| ATP synthase, gamma 1 | BC000931 | 509 | 208870_x_at | 1.01 | 0.718 | −1.03 | 0.182 |
| ATP synthase, gamma 1 | AV711183 | 509 | 213366_x_at | −1.02 | 0.650 | −1.03 | 0.213 |
| ATP synthase, gamma 1 | BG232034 | 509 | 214132_at | −1.12 | 0.428 | 1.05 | 0.404 |
| ATP synthase, O (oligomycin sensitivity conferring protein) | NM_001697 | 539 | 200818_at | −1.09 | 0.001 | −1.04 | 0.286 |
| ATP synthase, O (oligomycin sensitivity conferring protein) | S77356 | 539 | 216954_x_at | −1.16 | 0.001 | 1.01 | 0.738 |
| ATP synthase, s (factor B) | NM_015684 | 27109 | 206992_s_at | −1.08 | 0.079 | −1.09 | 0.093 |
| ATP synthase, s (factor B) | NM_015684 | 27109 | 206993_at | −1.15 | 0.014 | 1.08 | 0.222 |
| ATP synthase, s (factor B) | AW195882 | 27109 | 213995_at | −1.11 | 0.098 | 1.03 | 0.559 |

Abbreviations: ATP, adenosine triphosphate; BPD, bipolar disorder; COX, cytochrome c oxidase; Fe—S, iron-sulfur; ID, identification; NADH, reduced nicotinamide adenine dinucleotide; NC, normal control.
*Boldface type indicates statistical significance.

TABLE 8

Fifteen Mitochondrial Transcripts Used for Paired Comparisons

| gene | Locus Link ID | probe set | BPD: normal versus low glucose | | NC: normal versus low glucose | | ANOVA (diagnosis × glucose concentration) | |
|---|---|---|---|---|---|---|---|---|
| | | | fold change | p-value | fold change | p-value | F statistic | p-value |
| Complex I | | | | | | | | |
| NADH dehydrogenase 1 alpha, 5, 13 kDa | 4698 | 201304_at | −1.15 | 0.017 | 1.25 | 0.056 | 13.0 | 0.001 |
| NADH dehydrogenase 1 beta, 1, 7 kDa | 4707 | 206790_s_at | −1.04 | 0.177 | 1.07 | 0.080 | 6.9 | 0.012 |

TABLE 8-continued

Fifteen Mitochondrial Transcripts Used for Paired Comparisons

| gene | Locus Link ID | probe set | BPD: normal versus low glucose fold change | p-value | NC: normal versus low glucose fold change | p-value | ANOVA (diagnosis × glucose concentration) F statistic | p-value |
|---|---|---|---|---|---|---|---|---|
| Complex II | | | | | | | | |
| succinate dehydrogenase, D | 6392 | 202026_at | −1.09 | 0.074 | 1.07 | 0.205 | 5.0 | 0.032 |
| Complex III | | | | | | | | |
| ubiquinol-cyt c reductase binding protein | 7381 | 205849_s_at | −1.04 | 0.116 | 1.07 | 0.082 | 7.6 | 0.009 |
| ubiquinol-cyt c reductase binding protein | 7381 | 209065_at | −1.09 | 0.068 | 1.18 | 0.031 | 11.4 | 0.002 |
| ubiquinol-cyt c reductase core protein I | 7384 | 201903_at | 1.07 | 0.134 | −1.11 | 0.173 | 5.3 | 0.027 |
| Complex IV | | | | | | | | |
| COX 11 | 1353 | 211727_s_at | −1.04 | 0.452 | 1.14 | 0.007 | 5.4 | 0.026 |
| COX IV-1 | 1327 | 200086_s_at | −1.01 | 0.790 | 1.11 | 0.036 | 7.6 | 0.009 |
| COX VIIa-1 (muscle) | 1346 | 204570_at | 1.12 | 0.079 | −1.11 | 0.171 | 5.4 | 0.026 |
| COX VIIa-2 (liver) | 1347 | 201597_at | −1.06 | 0.104 | 1.1 | 0.081 | 7.3 | 0.010 |
| COX VIIc | 1350 | 217491_x_at | −1.02 | 0.500 | 1.08 | 0.067 | 5.4 | 0.026 |
| Complex V | | | | | | | | |
| ATP synthase, F0 complex, g | 10632 | 208745_at | −1.05 | 0.232 | 1.11 | 0.030 | 7.1 | 0.011 |
| ATP synthase, F0 complex, s (factor B) | 27109 | 206993_at | −1.12 | 0.032 | 1.02 | 0.780 | 5.9 | 0.020 |
| ATP synthase, F1 complex, epsilon subunit | 514 | 217801_at | −1.1 | 0.001 | 1.07 | 0.115 | 14.6 | 0.001 |
| ATP synthase, F1 complex, O (OSCP) | 539 | 216954_x_at | −1.07 | 0.042 | 1.16 | 0.021 | 6.4 | 0.016 |

Abbreviations: ANOVA, analysis of variance; ATP, adenosine triphosphate; BPD, bipolar disorder; COX, cytochrome c oxidase; cyt c, cytochrome c; ID, identification; NADH, reduced nicotinamide adenine dinucleotide; NC, normal control; OSCP, oligomycin sensitivity-conferring protein.
*Boldface type indicates statistical significance.

To determine whether a shift between B and T cells had taken place in any of the comparisons, the expression levels of 54 B-cell-specific transcripts and 77 T-cell-specific transcripts were examined (FIGS. 6A-6E, 7A-7D, and 8A-8E; Table 9) for transcripts). The percentage of individually regulated genes did not surpass the chance expectations in any of the comparisons (FIGS. 6A-6E; see FIGS. 1B(I)-1B(IV) for chance expectations), and the group of B-cell-specific (FIGS. 7A-7D) and T-cell-specific (FIGS. 8A-8D) transcripts was not significantly shifted. In addition, five marker genes for natural killer lymphocytes and five marker genes for monocytes were unchanged in all of the comparisons. Sixteen marker genes for granulocytes were examined as well; however, most were under the detection limit and none were affected by any condition.

TABLE 9

Transcripts Specific for B and T Cells Used for Analysis in FIGS. 6-8

| gene | GB Accession # | GeneID | Affymetrix probe set ID |
|---|---|---|---|
| B-Cell Markers | | | |
| B-cell CLL/lymphoma 10 | AF082283 | 8915 | 205263_at |
| B-cell CLL/lymphoma 11A (zinc finger protein) | AF080216 | 53335 | 210347_s_at |
| B-cell CLL/lymphoma 11A (zinc finger protein) | NM_018014 | 53335 | 219497_s_at |
| B-cell CLL/lymphoma 11A (zinc finger protein) | NM_018014 | 53335 | 219498_s_at |
| B-cell CLL/lymphoma 11B (zinc finger protein) | NM_022898 | 64919 | 219528_s_at |
| B-cell CLL/lymphoma 2 | M13994 | 596 | 203684_s_at |
| B-cell CLL/lymphoma 2 | NM_000633 | 596 | 203685_at |
| B-cell CLL/lymphoma 3 | NM_005178 | 602 | 204908_s_at |
| B-cell CLL/lymphoma 6 (zinc finger protein 51) | NM_001706 | 604 | 203140_at |
| B-cell CLL/lymphoma 6 (zinc finger protein 51) | S67779 | 604 | 215990_s_at |

TABLE 9-continued

Transcripts Specific for B and T Cells Used for Analysis in FIGS. 6-8

| gene | GB Accession # | GeneID | Affymetrix probe set ID |
|---|---|---|---|
| B-cell CLL/lymphoma 7A | NM_020993 | 605 | 203795_s_at |
| B-cell CLL/lymphoma 7A | NM_020993 | 605 | 203796_s_at |
| B-cell CLL/lymphoma 7B | NM_001707 | 9275 | 202518_at |
| B-cell CLL/lymphoma 7C | NM_004765 | 9274 | 219072_at |
| B-cell CLL/lymphoma 9 | NM_004326 | 607 | 204129_at |
| B-cell linker | NM_013314 | 29760 | 207655_s_at |
| B-cell receptor-associated protein 29 | NM_018844 | 55973 | 205084_at |
| B-cell receptor-associated protein 29 | AL583687 | 55973 | 217657_at |
| B-cell receptor-associated protein 29 | AI393960 | 55973 | 217662_x_at |
| B-cell receptor-associated protein 31 | NM_005745 | 10134 | 200837_at |
| B-cell scaffold protein with ankyrin repeats 1 | NM_017935 | 55024 | 219667_s_at |
| B-cell translocation gene 1, anti-proliferative | AL535380 | 694 | 200920_s_at |
| B-cell translocation gene 1, anti-proliferative | NM_001731 | 694 | 200921_s_at |
| cardiotrophin-like cytokine factor 1 | NM_013246 | 23529 | 219500_at |
| CD19 antigen | NM_001770 | 930 | 206398_s_at |
| CD22 antigen | NM_001771 | 4099, 933 | 204581_at |
| CD40 antigen (TNF receptor superfamily member 5) | NM_001250 | 958 | 205153_s_at |
| CD40 antigen (TNF receptor superfamily member 5) | BF664114 | 958 | 215346_at |
| CD40 antigen (TNF receptor superfamily member 5) | X60592 | 958 | 35150_at |
| CD48 antigen (B-cell membrane protein) | NM_001778 | 962 | 204118_at |
| CD80 antigen (CD28 antigen ligand 1, B7-1 antigen) | NM_005191 | 941 | 207176_s_at |
| CD83 antigen (activated B lymphocytes, immunoglobulin) | NM_004233 | 9308 | 204440_at |
| CD86 antigen (CD28 antigen ligand 2, B7-2 antigen) | BG236280 | 942 | 205685_at |
| CD86 antigen (CD28 antigen ligand 2, B7-2 antigen) | NM_006889 | 942 | 205686_s_at |
| CD86 antigen (CD28 antigen ligand 2, B7-2 antigen) | L25259 | 942 | 210895_s_at |
| interleukin 4 receptor | NM_000418 | 3566 | 203233_at |
| membrane-spanning 4-domains, subfamily A, member 1 | BC002807 | 931 | 210356_x_at |
| membrane-spanning 4-domains, subfamily A, member 1 | X12530 | 931 | 217418_x_at |
| musculin (activated B-cell factor-1) | AF060154 | 9242 | 209928_s_at |
| Paired box gene 5 (B-cell lineage specific activator) | BF510692 | 5079 | 221969_at |
| pre-B-cell colony enhancing factor 1 | NM_005746 | 10135 | 217738_at |
| pre-B-cell colony enhancing factor 1 | NM_005746 | 10135 | 217739_s_at |
| Pre-B-cell leukemia transcription factor 1 | BF967998 | 5087 | 212151_at |
| pre-B-cell leukemia transcription factor 2 | BE397715 | 5089 | 202875_s_at |
| pre-B-cell leukemia transcription factor 2 | NM_002586 | 5089 | 202876_s_at |
| pre-B-cell leukemia transcription factor 2 | BC003111 | 5089 | 211096_at |
| pre-B-cell leukemia transcription factor 2 | BC003111 | 5089 | 211097_s_at |
| pre-B-cell leukemia transcription factor 3 | NM_006195 | 5090 | 204082_at |
| pre-B-cell leukemia transcription factor interacting protein 1 | NM_020524 | 57326 | 207838_x_at |
| pre-B-cell leukemia transcription factor interacting protein 1 | BF344265 | 57326 | 212259_s_at |
| Pre-B-cell leukemia transcription factor interacting protein 1 | AI348545 | 57326 | 214176_s_at |
| pre-B-cell leukemia transcription | AI935162 | 57326 | 214177_s_at |

TABLE 9-continued

Transcripts Specific for B and T Cells Used for Analysis in FIGS. 6-8

| gene | GB Accession # | GeneID | Affymetrix probe set ID |
|---|---|---|---|
| factor interacting protein 1 | | | |
| prohibitin 2 | NM_007273 | 11331 | 201600_at |
| tumor necrosis factor receptor superfamily, member 17 | NM_001192 | 608 | 206641_at |
| T-cell Markers | | | |
| CD2 antigen (p50), sheep red blood cell receptor | NM_001767 | 914 | 205831_at |
| CD28 antigen (Tp44) | NM_006139 | 940 | 206545_at |
| CD28 antigen (Tp44) | AF222341 | 940 | 211856_x_at |
| CD28 antigen (Tp44) | AF222343 | 940 | 211861_x_at |
| CD3Z antigen, zeta polypeptide (TiT3 complex) | J04132 | 919 | 210031_at |
| CD4 antigen (p55) | U47924 | 920 | 203547_at |
| CD5 antigen (p56-62) | NM_014207 | 921 | 206485_at |
| CD6 antigen | NM_006725 | 923 | 208602_x_at |
| CD6 antigen | U66145 | 923 | 211893_x_at |
| CD6 antigen | U66146 | 923 | 211900_x_at |
| CD6 antigen | AW134823 | 923 | 213958_at |
| CD69 antigen (p60, early T-cell activation antigen) | L07555 | 969 | 209795_at |
| CD8 antigen, alpha polypeptide (p32) | AW006735 | 925 | 205758_at |
| cutaneous T-cell lymphoma-associated antigen 1 | NM_022663 | 64693 | 220957_at |
| expressed in T-cells and eosinophils in atopic dermatitis | AB020694 | 23197 | 212106_at |
| expressed in T-cells and eosinophils in atopic dermatitis | AB020694 | 23197 | 212108_at |
| frequently rearranged in advanced T-cell lymphomas | NM_005479 | 10023 | 219889_at |
| frequently rearranged in advanced T-cell lymphomas 2 | AB045118 | 23401 | 209864_at |
| granulysin | NM_006433 | 10578 | 205495_s_at |
| granulysin | M85276 | 10578 | 37145_at |
| human T-cell leukemia virus enhancer factor | NM_002158 | 3344 | 206708_at |
| IL2-inducible T-cell kinase | D13720 | 3702 | 211339_s_at |
| inducible T-cell co-stimulator | AB023135 | 29851 | 210439_at |
| inducible T-cell co-stimulator ligand | AL355690 | 23308 | 211197_s_at |
| mal, T-cell differentiation protein | NM_002371 | 4118 | 204777_s_at |
| mature T-cell proliferation 1 | NM_014221 | 4515 | 205106_at |
| mature T-cell proliferation 1 | BC002600 | 4515 | 210212_x_at |
| mature T-cell proliferation 1 | Z24459 | 4515 | 216862_s_at |
| pre T-cell antigen receptor alpha | U36759 | 171558 | 211252_x_at |
| pre T-cell antigen receptor alpha | AL035587 | 171558 | 215492_x_at |
| Rearranged T-cell receptor alpha chain mRNA, variable region | AE000659 | | 217412_at |
| sirtuin (silent mating type information regulation 2 homolog) 6 | NM_016539 | 51548 | 219613_s_at |
| T cell receptor alpha constant | M12959 | 28755 | 209670_at |
| T cell receptor alpha locus | L34703 | 6955 | 211902_x_at |
| T cell receptor alpha locus | AW873544 | 6955 | 215769_at |
| T cell receptor alpha locus | X61070 | 6955 | 217056_at |
| T cell receptor alpha locus | AE000659 | 6955 | 217394_at |
| T cell receptor alpha locus | AW966434 | 28517, 28663, 28738, 28755, 348035, 6955 | 215524_x_at |
| T cell receptor alpha locus | M15565 | 28517, 28663, 28738, 28755, 6955 | 210972_x_at |
| T cell receptor alpha locus | M12423 | 28755, 6955 | 209671_x_at |
| T cell receptor alpha locus, T cell receptor delta locus | X72501 | 6955, 6964 | 216191_s_at |
| T cell receptor alpha variable 20 | BF976764 | 28663 | 215796_at |
| T cell receptor associated transmembrane adaptor 1 | AJ240085 | 50852 | 217147_s_at |
| T cell receptor beta constant 1 | M15564 | 28568, 28639 | 210915_x_at |
| T cell receptor gamma constant 2 | M30894 | 6967 | 211144_x_at |
| T cell receptor gamma constant 2 | M16768 | 442532, 442670, 445347, 6967, 6983 | 209813_x_at |
| T cell receptor gamma constant 2 | M13231 | 442532, 442670, 445347, 6967, 6983 | 215806_x_at |
| T cell receptor gamma constant 2 | M27331 | 442532, 442670, 445347, 6967, 6983 | 216920_s_at |

TABLE 9-continued

Transcripts Specific for B and T Cells Used for Analysis in FIGS. 6-8

| gene | GB Accession # | GeneID | Affymetrix probe set ID |
|---|---|---|---|
| T cell receptor V alpha gene segment V-alpha-w23, clone IGRa01 | AA284903 | | 216133_at |
| T cell receptor V alpha gene segment V-alpha-w24, clone IGRa02 | AE000659 | | 217397_at |
| Tax1 (human T-cell leukemia virus type I) binding protein 1 | AF090891 | 8887 | 200976_s_at |
| Tax1 (human T-cell leukemia virus type I) binding protein 1 | AF090891 | 8887 | 200977_s_at |
| Tax1 (human T-cell leukemia virus type I) binding protein 1 | AI935415 | 8887 | 213786_at |
| Tax1 (human T-cell leukemia virus type I) binding protein 3 | AF234997 | 30851 | 209154_at |
| Tax1 (human T-cell leukemia virus type I) binding protein 3 | AK001327 | 30851 | 215459_at |
| Tax1 (human T-cell leukemia virus type I) binding protein 3 | AK001327 | 30851 | 215464_s_at |
| T-cell acute lymphocytic leukemia 1 | NM_003189 | 6886 | 206283_s_at |
| T-cell immunomodulatory protein | NM_030790 | 81533 | 221449_s_at |
| T-cell leukemia translocation altered gene | NM_022171 | 6988 | 203054_s_at |
| T-cell leukemia/lymphoma 1A | BC003574 | 8115 | 209995_s_at |
| T-cell leukemia/lymphoma 1A | X82240 | 8115 | 39318_at |
| T-cell lymphoma invasion and metastasis 1 | NM_003253 | 7074 | 206409_at |
| T-cell lymphoma invasion and metastasis 1 | U90902 | 7074 | 213135_at |
| T-cell receptor active alpha-chain V-region | L34698 | | 211667_x_at |
| T-cell receptor active alpha-chain V-region | AE000659 | | 217170_at |
| T-cell receptor active beta-chain (V10-D-J-C) mRNA, clone PL3.9 | L48728 | | 216857_at |
| T-cell receptor alpha chain (TCRA) | X61079 | | 217063_x_at |
| TCR V alpha 14.1/J alpha 32/C alpha | X61072 | | 216540_at |
| transcription factor 7 (T-cell specific, HMG-box) | AW027359 | 6932 | 205254_x_at |
| transcription factor 7 (T-cell specific, HMG-box) | NM_003202 | 6932 | 205255_x_at |
| transcription factor 7-like 2 (T-cell specific, HMG-box) | AI703074 | 6934 | 212761_at |
| transcription factor 7-like 2 (T-cell specific, HMG-box) | AI375916 | 6934 | 212762_s_at |
| transcription factor 7-like 2 (T-cell specific, HMG-box) | AV721430 | 6934 | 216035_x_at |
| transcription factor 7-like 2 (T-cell specific, HMG-box) | AA664011 | 6934 | 216037_x_at |
| transcription factor 7-like 2 (T-cell specific, HMG-box) | AJ270770 | 6934 | 216511_s_at |
| TSPY-like 2 | NM_022117 | 64061 | 218012_at |
| Vac14 homolog | U25801 | 55697 | 216407_at |

Abbreviations:
CLL, chronic lymphocytic leukemia;
HMG, high-mobility group;
ID, identification;
IL2, interleukin 2;
mRNA, messenger RNA;
NA, not available;
TNF, tumor necrosis factor;
TSPY, testis-specific protein, Y-linked;
Vac, vacuole morphology.

Almost all BPD patients were on medication (see FIG. 2), thus raising the possibility of medication effects. This concern was alleviated by the fact that no single medication was present in more than 30% of all BPD patients, and medications ranged from lithium, to valproic acid (VA), anticonvulsants, antidepressants, and antipsychotics. We found no affiliation of electron transport transcript expression levels with medication (FIGS. 4A-4E). Therefore, if the data reflect a medication effect as opposed to an effect intrinsic to the disease, this effect must be common to all medications used to treat BPD and might represent a common therapeutic pathway. The likelihood for a medication effect is limited by the facts that (a) both the fresh (uncultured) lymphocytes and the normal glucose cultured lymphocytes showed no difference between controls and BPD, and (b) the lymphocytes in culture were washed three times before plating and then cultured for five days in the absence of any drugs. Thus, we believe that the differences observed between the BPD patients and controls is due to disease rather than due to medication.

All patents, patent applications, and publications mentioned in this specification are herein incorporated by reference, to the same extent as if each independent patent, patent application, or publication was specifically and individually indicated to be incorporated by reference.

What is claimed is:

1. A method for diagnosing bipolar disorder in a subject, said method comprising the steps:
   (a) obtaining a cell sample from said subject, wherein said sample is a blood sample;
   (b) subjecting a cell from said sample to stress; and
   (c) measuring the level of expression in said cell of at least three nuclear encoded mitochondrial energy metabolism nucleic acids or polypeptides, wherein a decrease in said level of expression, as compared to the expression in a cell that is subjected to said stress from a sample obtained from a control subject, is indicative of said subject having bipolar disorder, wherein at least three of said nucleic acids or polypeptides are selected from the group consisting of NADH dehydrogenase (ubiquinone) 1 alpha subcomplex, 5, 13 kDa (NDUFA5; Entrez Gene ID:4698); NADH dehydrogenase (ubiquinone) 1 alpha subcomplex, 6, 14 kDa (NDUFA6; Entrez Gene ID:4700); NADH dehydrogenase (ubiquinone) 1 beta subcomplex, 1, 7 kDa (NDUFB1; Entrez Gene ID: 4707); ubiquinol-cytochrome c reductase binding protein (UQCRB; Entrez Gene ID: 7381); ubiquinol-cytochrome c reductase core protein II (UQCRC2; Entrez Gene ID: 7385); ubiquinol-cytochrome c reductase hinge protein (UQCRH; Entrez Gene ID: 7388); cytochrome c oxidase subunit IV isoform 1 (COX4I1; Entrez Gene ID: 1327); cytochrome c oxidase subunit VIIa polypeptide 2 like (COX7A2L; Entrez Gene ID: 9167); cytochrome c oxidase subunit VIIc (COX7C; Entrez Gene ID: 1350); COX11 homolog, cytochrome c oxidase assembly protein (yeast) (COX11; Entrez Gene ID: 1353); COX15 homolog, cytochrome c oxidase assembly protein (yeast) (COX15: Entrez Gene ID: 1355); ATP synthase, H+ transporting, mitochondrial F0 complex, subunit C2 (subunit 9) (ATP5G2; Entrez Gene ID: 517); ATP synthase, H+ transporting, mitochondrial F0 complex, subunit G (ATP5L; Gene ID: 10632); ATP synthase, H+ transporting, mitochondrial F1 complex, O subunit (ATP5O; Entrez Gene ID No: 539); and ATP synthase, H+ transporting, mitochondrial F0 complex, subunit s (factor B) (ATP5S; Entrez Gene ID No: 27109).

2. A method for diagnosing bipolar disorder in a subject, said method comprising the steps:
   (a) obtaining a cell sample from said subject, wherein said cell sample comprises a lymphocyte;
   (b) subjecting a cell from said sample to stress; and
   (c) measuring the level of expression in said cell of at least three nuclear encoded mitochondrial energy metabolism nucleic acids or polypeptides, wherein a decrease in said level of expression, as compared to the expression in a cell that is subjected to said stress from a sample obtained from a control subject, is indicative of said subject having bipolar disorder, wherein at least three of said nucleic acids or polypeptides are selected from the group consisting of NADH dehydrogenase (ubiquinone) 1 alpha subcomplex, 5, 13 kDa (NDUFA5; Entrez Gene ID:4698); NADH dehydrogenase (ubiquinone) 1 alpha subcomplex, 6, 14 kDa (NDUFA6; Entrez Gene ID:4700); NADH dehydrogenase (ubiquinone) 1 beta subcomplex, 1, 7 kDa (NDUFB1; Entrez Gene ID: 4707); ubiquinol-cytochrome c reductase binding protein (UQCRB; Entrez Gene ID: 7381); ubiquinol-cytochrome c reductase core protein II (UQCRC2; Entrez Gene ID: 7385); ubiquinol-cytochrome c reductase hinge protein (UQCRH; Entrez Gene ID: 7388); cytochrome c oxidase subunit IV isoform 1 (COX4I1; Entrez Gene ID: 1327); cytochrome c oxidase subunit VIIa polypeptide 2 like (COX7A2L; Entrez Gene ID: 9167); cytochrome c oxidase subunit VIIc (COX7C; Entrez Gene ID: 1350); COX11 homolog, cytochrome c oxidase assembly protein (yeast) (COX11; Entrez Gene ID: 1353); COX15 homolog, cytochrome c oxidase assembly protein (yeast) (COX15: Entrez Gene ID: 1355); ATP synthase, H+ transporting, mitochondrial F0 complex, subunit C2 (subunit 9) (ATP5G2; Entrez Gene ID: 517); ATP synthase, H+ transporting, mitochondrial F0 complex, subunit G (ATP5L; Gene ID: 10632); ATP synthase, H+ transporting, mitochondrial F1 complex, O subunit (ATP5O; Entrez Gene ID No: 539); and ATP synthase, H+ transporting, mitochondrial F0 complex, subunit s (factor B) (ATP5S; Entrez Gene ID No: 27109).

3. A method for diagnosing bipolar disorder in a subject, said method comprising the steps:
(a) obtaining a cell sample from said subject;
(b) subjecting a cell from said sample to glucose stress; and
(c) measuring the level of expression in said cell of at least three nuclear encoded mitochondrial energy metabolism nucleic acids or polypeptides, wherein a decrease in said level of expression, as compared to the expression in a cell that is subjected to said stress from a sample obtained from a control subject, is indicative of said subject having bipolar disorder, wherein at least three of said nucleic acids or polypeptides are selected from the group consisting of NADH dehydrogenase (ubiquinone) 1 alpha subcomplex, 5, 13 kDa (NDUFA5; Entrez Gene ID:4698); NADH dehydrogenase (ubiquinone) 1 alpha subcomplex, 6, 14 kDa (NDUFA6; Entrez Gene ID:4700); NADH dehydrogenase (ubiquinone) 1 beta subcomplex, 1, 7 kDa (NDUFB1; Entrez Gene ID: 4707); ubiquinol-cytochrome c reductase binding protein (UQCRB; Entrez Gene ID: 7381); ubiquinol-cytochrome c reductase core protein II (UQCRC2; Entrez Gene ID: 7385); ubiquinol-cytochrome c reductase hinge protein (UQCRH; Entrez Gene ID: 7388); cytochrome c oxidase subunit IV isoform 1 (COX4I1; Entrez Gene ID: 1327); cytochrome c oxidase subunit VIIa polypeptide 2 like (COX7A2L; Entrez Gene ID: 9167); cytochrome c oxidase subunit VIIc (COX7C; Entrez Gene ID: 1350); COX11 homolog, cytochrome c oxidase assembly protein (yeast) (COX11; Entrez Gene ID: 1353); COX15 homolog, cytochrome c oxidase assembly protein (yeast) (COX15: Entrez Gene ID: 1355); ATP synthase, H+ transporting, mitochondrial F0 complex, subunit C2 (subunit 9) (ATP5G2; Entrez Gene ID: 517); ATP synthase, H+ transporting, mitochondrial F0 complex, subunit G (ATP5L; Gene ID: 10632); ATP synthase, H+ transporting, mitochondrial F1 complex, O subunit (ATP5O; Entrez Gene ID No: 539); and ATP synthase, H+ transporting, mitochondrial F0 complex, subunit s (factor B) (ATP5S; Entrez Gene ID No: 27109).

4. A method for diagnosing bipolar disorder in a subject, said method comprising the steps:
(a) obtaining a lymphocyte from said subject;
(b) culturing said lymphocyte under glucose stress; and
(c) measuring the level of expression in said lymphocyte of at least 15 nuclear encoded mitochondrial energy metabolism nucleic acids, wherein said nucleic acids comprise ATP synthase, mitochondrial F1 complex, O subunit (ATP5O; Entrez Gene ID: 539); cytochrome c oxidase subunit IV isoform 1 (COX4I1; Entrez Gene ID: 1327); and ubiquinol-cytochrome c reductase binding protein (UQCRB; Entrez Gene ID: 7381) and wherein a decrease in said level of expression, as compared to the expression in a lymphocyte obtained from a control subject that is cultured under glucose stress, is indicative of said subject having bipolar disorder.

5. A method for diagnosing bipolar disorder in a subject, said method comprising the steps:
(a) obtaining a lymphocyte from said subject;
(b) culturing said lymphocyte under glucose stress; and
(c) measuring the level of expression in said lymphocyte of at least 15 nuclear encoded mitochondrial energy metabolism nucleic acids of claim 4, wherein said nucleic acids comprise ATP synthase, mitochondrial F1 complex, O subunit (ATP5O; Entrez Gene ID: 539); cytochrome c oxidase subunit IV isoform 1 (COX4I1; Entrez Gene ID: 1327); ubiquinol-cytochrome c reductase binding protein (UQCRB; Entrez Gene ID: 7381); ATP synthase, H+ transporting, mitochondrial F0 complex, subunit s (factor B) (ATP5S; Entrez Gene ID: 27109); and ubiquinol-cytochrome c reductase core protein II (UQCRC2; Entrez Gene ID: 7385) and wherein a decrease in said level of expression, as compared to the expression in a lymphocyte obtained from a control subject that is cultured under glucose stress, is indicative of said subject having bipolar disorder.

* * * * *

```
                        SEQUENCE LISTING

<160> NUMBER OF SEQ ID NOS: 14

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
cgagcaattt ccacctctgt                                              20

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
tgggattgga actgtgtttg                                              20

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
tgttgttgga ccatgtgtga                                              20

<210> SEQ ID NO 4
<211> LENGTH: 19
<212> TYPE: DNA
<213> ORGANISM: Artificial Sequence
<220> FEATURE:
<223> OTHER INFORMATION: Primer

<400> SEQUENCE: 4
ctgaaggaac ccaaagtgg                                               19

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
ctcccattct tccacctttg                                              20
```

```
<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
gggcgagtct tcatctaagg                                               20

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
cattcgtgag gatgacaaca                                               20

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
caggaggcct tctccttctc                                               20

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
tcacatggca aagaggatga                                               20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
gcgggctaaa cagacgtgta                                               20

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
gaaaaggcag aaacgactcc                                               20

<210> SEQ ID NO 12
<211> LENGTH: 18
<212> TYPE: DNA
<213> ORGANISM: Artificial Sequence
<220> FEATURE:
<223> OTHER INFORMATION: Primer
```

-continued

```
<400> SEQUENCE: 12
gtccaccacc ctgttgct                                                 18

<210> SEQ ID NO 13
<211> LENGTH: 21
<212> TYPE: DNA
<213> ORGANISM: Artificial Sequence
<220> FEATURE:
<223> OTHER INFORMATION: Primer

<400> SEQUENCE: 13
aatggtctgt gtgaagggag a                                             21

<210> SEQ ID NO 14
<211> LENGTH: 21
<212> TYPE: DNA
<213> ORGANISM: Artificial Sequence
<220> FEATURE:
<223> OTHER INFORMATION: Primer

<400> SEQUENCE: 14
cagcaacaag tccaggtaag c                                             21
```